United States Patent [19]
Markland, Jr. et al.

[11] Patent Number: 5,951,981
[45] Date of Patent: Sep. 14, 1999

[54] THROMBOLYTIC AGENTS WITH ANTITHROMBOTIC ACTIVITY

[75] Inventors: Francis S. Markland, Jr., Manhattan Beach, Calif.; Larry R. Bush, Exeter, N.H.; Stephen Swenson, Arcadia, Calif.; Eladio Flores Sanchez, Belo Horizonte-ma, Brazil

[73] Assignee: Diatide, Inc., Londonderry, N.H.

[21] Appl. No.: 08/753,781

[22] Filed: Dec. 2, 1996

[51] Int. Cl.$^6$ .......................... A61K 38/54; A61K 38/46; C12N 9/96; C12N 9/48
[52] U.S. Cl. ..................... 424/94.67; 424/94.3; 435/212; 435/188
[58] Field of Search ..................................... 435/188, 212, 435/215, 216, 217; 424/94.64, 94.67, 94.3

[56] References Cited

U.S. PATENT DOCUMENTS

| | | | |
|---|---|---|---|
| 4,610,879 | 9/1986 | Markland, Jr. et al. | 424/94.67 |
| 4,790,988 | 12/1988 | Mehta et al. | 424/94.64 |
| 5,116,613 | 5/1992 | Haber et al. | 424/178.1 |
| 5,187,098 | 2/1993 | Malke et al. | 435/320.1 |
| 5,237,050 | 8/1993 | Boyle et al. | 530/350 |
| 5,260,060 | 11/1993 | Markland, Jr. et al. | 424/94.67 |
| 5,288,490 | 2/1994 | Budzynski et al. | 424/94.64 |
| 5,317,097 | 5/1994 | Miller et al. | 536/24.31 |
| 5,328,898 | 7/1994 | Greenberg | 514/12 |
| 5,504,001 | 4/1996 | Foster | 435/219 |
| 5,632,986 | 5/1997 | Tait et al. | 424/94.64 |

FOREIGN PATENT DOCUMENTS

| | | |
|---|---|---|
| 0 323 722 A1 | 7/1989 | European Pat. Off. . |
| 89/00051 | 1/1989 | WIPO . |
| 90/11783 | 10/1990 | WIPO . |
| 94/01543 | 1/1994 | WIPO . |

OTHER PUBLICATIONS

Laudano et al., Biochemistry, 19(5), "Studies on Synthetic Peptides that Bind to Fibrinogen and Prevent Fibrin Polymerization. Structural Requirements, Number of Binding Sites, and Species Differences", pp. 1013–1019, Mar. 1980.

Hua, et al., (1996) "Characterization of a Recombinant Chimeric Plasminogen Activator Composed of Gly–Pro–Arg–Pro Tetrapeptide and Truncated Urokinase–Type Plasminogen Activator expressed in *Escherichia coli*" Biochemical and Biophysical Research Communications 222, 576–583.

Lubin, et al., (1992) "Strategies for the Design of Novel Thrombolytic and Antithrombolytic Agents" Trends Cardiovasc Med 2, 84–89.

Markland, (1996) "Fibrolase, An Active Trhombolytic Enzyme in Arterial and Venous Thrombosis Model Systems" Natural Toxins II, 427–438.

Andrieux et al. (1993) J. Biol. Chem., 264(16), "Amino Acid Sequences in Fibrinogen Mediating its Interaction with Its Platelet Receptor, GPllbllla", pp. 9258–9265.

Robbins et al. (1986) Biochemistry, 25(12), "Covalent Molecular Weight~92000 Hybrid Plasminogen Activator Derived from Human Plasmin Amino–Terminal and Urokinase Carboxyl–Terminal Domains", pp. 3603–3611.

*Primary Examiner*—Jon P. Weber
*Attorney, Agent, or Firm*—Patricia A. McDaniels; Kevin E. Noonan

[57] ABSTRACT

This invention provides thrombolytic agents and methods for making and using thrombolytic agents. Specifically, the invention provides thrombolytic agents comprising a thrombolytic proteinase and a specific binding peptide that specifically binds at the site of blood clots and thrombi in vivo. The invention particularly provides chemically crosslinked conjugates of a thrombolytic proteinase and a plurality of specific binding peptide. Methods for producing such chemically crosslinked conjugates and methods for using such conjugates for eliminating thrombi in vivo to alleviate pathological conditions caused thereby are also provided. The preferred thrombolytic proteinase in the conjugate is fibrolase obtainable from *Agkistrodon contortrix confortrix* venom.

7 Claims, 8 Drawing Sheets

N—SUCCINIMIDYL—3—[2-PYRIDYLDITHIO] PROPIONATE (SPDP)
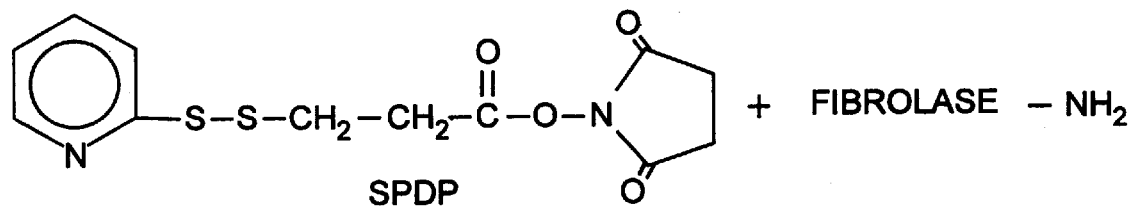
$\downarrow$ pH>7
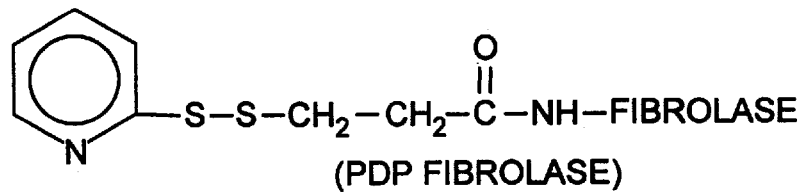
+
RGD PEPTIDE-SH
$\downarrow$
RGD PEPTIDE—S—S—CH$_2$—CH$_2$—CO—NH—FIBROLASE
FIG. 3

SULFOUCCINIMIDYL 6-[α-METHYL-α-(2-PYRIDYLDITHIO) TOLUAMIDO] HEXONATE)
(S-SMPT)

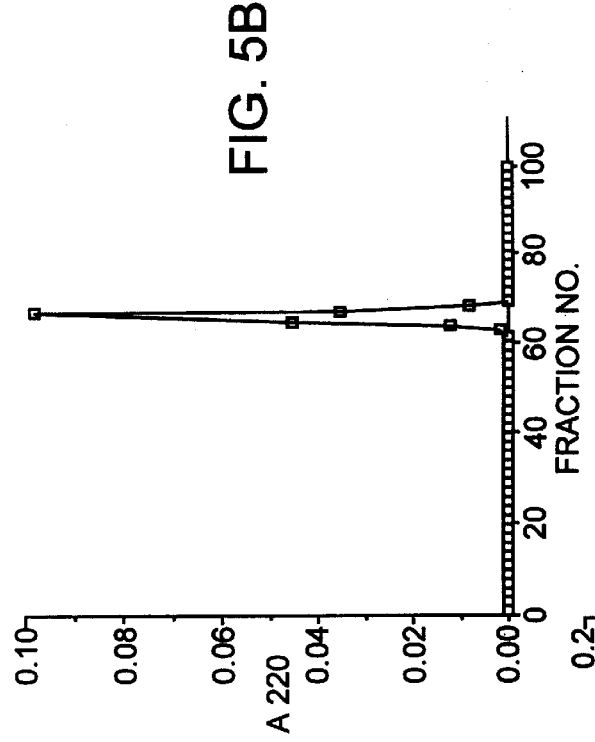
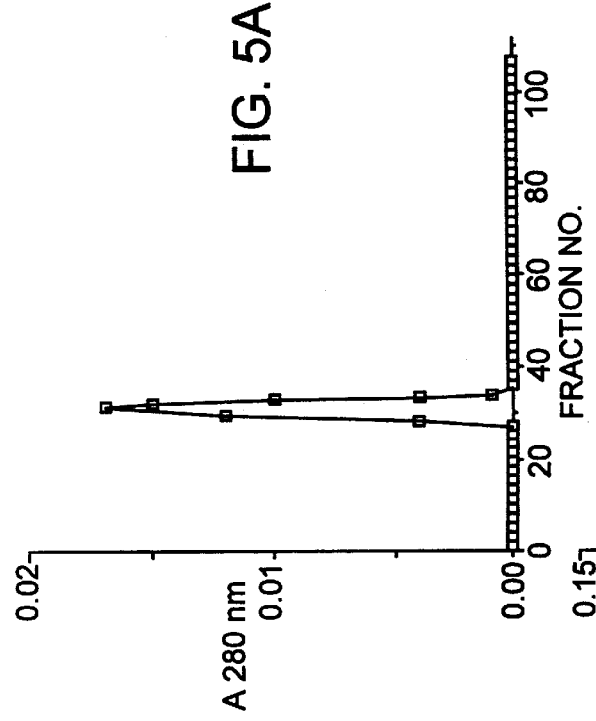
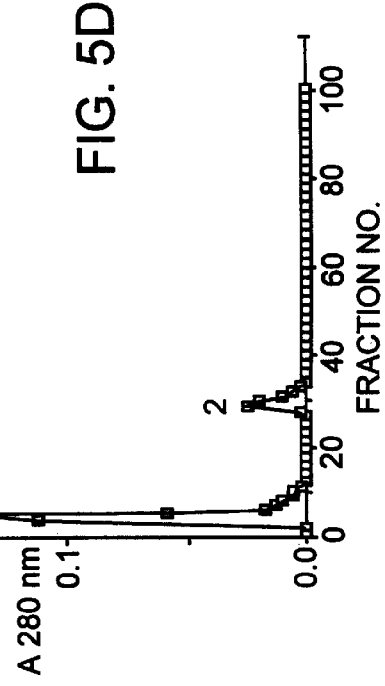
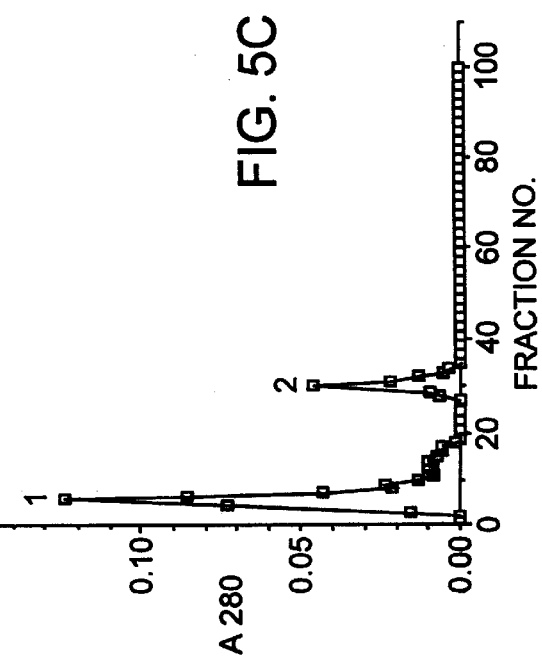

SEQUENCE LISTING

<160> NUMBER OF SEQ ID NOS: 40

<210> SEQ ID NO 1

```
<211> LENGTH: 12
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 1

His His Leu Gly Gly Ala Lys Gln Ala Gly Asp Val
 1               5                  10

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 2

Gly Pro Arg Pro
 1

<210> SEQ ID NO 3
<211> LENGTH: 10
<212> TYPE: PRT
<213> ORGANISM: Artificial Sequence
<220> FEATURE:
<221> NAME/KEY: MOD_RES
<222> LOCATION: (1)
<223> OTHER INFORMATION: acetamidomethyl
<220> FEATURE:
<221> NAME/KEY: MOD_RES
<222> LOCATION: (3)
<223> OTHER INFORMATION: acetamidomethyl
<220> FEATURE:
<223> OTHER INFORMATION: Description of Artificial Sequence:synthetic
      peptide

<400> SEQUENCE: 3

Cys Gly Cys Gly Gly Arg Gly Asp Ser Cys
 1               5                  10

<210> SEQ ID NO 4
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: acetamidomethyl
<220> FEATURE:
<221> NAME/KEY: MOD_RES
<222> LOCATION: (3)
<223> OTHER INFORMATION: acetamidomethyl
<220> FEATURE:
<223> OTHER INFORMATION: Description of Artificial Sequence:synthetic
      peptide

<400> SEQUENCE: 4

Cys Gly Cys Gly Gly Arg Gly Asp Gly Gly Arg Gly Asp Ser Cys
 1               5                  10                  15

<210> SEQ ID NO 5
<211> LENGTH: 20
<212> TYPE: PRT
<213> ORGANISM: Artificial Sequence
<220> FEATURE:
<221> NAME/KEY: MOD_RES
<222> LOCATION: (1)
<223> OTHER INFORMATION: acetamidomethyl
<220> FEATURE:
```

```
<221> NAME/KEY: MOD_RES
<222> LOCATION: (3)
<223> OTHER INFORMATION: acetamidomethyl
<220> FEATURE:
<223> OTHER INFORMATION: Description of Artificial Sequence:synthetic
      peptide

<400> SEQUENCE: 5

Cys Gly Cys Gly Gly Arg Gly Asp Gly Gly Arg Gly Asp Gly Gly Arg
 1               5                  10                  15

Gly Asp Ser Cys
            20

<210> SEQ ID NO 6
<211> LENGTH: 16
<212> TYPE: PRT
<213> ORGANISM: Artificial Sequence
<220> FEATURE:
<221> NAME/KEY: MOD_RES
<222> LOCATION: (1)
<223> OTHER INFORMATION: acetamidomethyl
<220> FEATURE:
<221> NAME/KEY: MOD_RES
<222> LOCATION: (3)
<223> OTHER INFORMATION: acetamidomethyl
<220> FEATURE:
<223> OTHER INFORMATION: Description of Artificial Sequence:synthetic
      peptide

<400> SEQUENCE: 6

Cys Gly Cys Arg Arg Arg Arg Arg Arg Arg Arg Arg Gly Asp Val Cys
 1               5                  10                  15

<210> SEQ ID NO 7
<211> LENGTH: 10
<212> TYPE: PRT
<213> ORGANISM: Artificial Sequence
<220> FEATURE:
<221> NAME/KEY: MOD_RES
<222> LOCATION: (8)
<223> OTHER INFORMATION: acetamidomethyl
<220> FEATURE:
<221> NAME/KEY: MOD_RES
<222> LOCATION: (10)
<223> OTHER INFORMATION: acetamidomethyl
<220> FEATURE:
<221> NAME/KEY: MOD_RES
<222> LOCATION: (10)
<223> OTHER INFORMATION: AMIDATION
<220> FEATURE:
<223> OTHER INFORMATION: Description of Artificial Sequence:synthetic
      peptide

<400> SEQUENCE: 7

Cys Gly Arg Gly Asp Val Lys Cys Gly Cys
 1               5                  10

<210> SEQ ID NO 8
<211> LENGTH: 9
<212> TYPE: PRT
<213> ORGANISM: Artificial Sequence
<220> FEATURE:
<221> NAME/KEY: MOD_RES
<222> LOCATION: (7)
<223> OTHER INFORMATION: acetamidomethyl
<220> FEATURE:
<221> NAME/KEY: MOD_RES
<222> LOCATION: (9)
<223> OTHER INFORMATION: acetamidomethyl
<220> FEATURE:
<221> NAME/KEY: MOD_RES
<222> LOCATION: (9)
<223> OTHER INFORMATION: AMIDATION
```

```
<220> FEATURE:
<223> OTHER INFORMATION: Description of Artificial Sequence:synthetic
      peptide

<400> SEQUENCE: 8

Cys Gly Arg Gly Asp Val Cys Gly Cys
 1               5

<210> SEQ ID NO 9
<211> LENGTH: 14
<212> TYPE: PRT
<213> ORGANISM: Artificial Sequence
<220> FEATURE:
<221> NAME/KEY: MOD_RES
<222> LOCATION: (12)
<223> OTHER INFORMATION: acetamidomethyl
<220> FEATURE:
<221> NAME/KEY: MOD_RES
<222> LOCATION: (14)
<223> OTHER INFORMATION: acetamidomethyl
<220> FEATURE:
<221> NAME/KEY: MOD_RES
<222> LOCATION: (14)
<223> OTHER INFORMATION: AMIDATION
<220> FEATURE:
<223> OTHER INFORMATION: Description of Artificial Sequence:synthetic
      peptide

<400> SEQUENCE: 9

Cys Gly Arg Gly Asp Val Arg Gly Asp Phe Lys Cys Gly Cys
 1               5                  10

<210> SEQ ID NO 10
<211> LENGTH: 13
<212> TYPE: PRT
<213> ORGANISM: Artificial Sequence
<220> FEATURE:
<221> NAME/KEY: MOD_RES
<222> LOCATION: (11)
<223> OTHER INFORMATION: acetamidomethyl
<220> FEATURE:
<221> NAME/KEY: MOD_RES
<222> LOCATION: (13)
<223> OTHER INFORMATION: acetamidomethyl
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence:synthetic
      peptide

<400> SEQUENCE: 10

Cys Gly Arg Gly Asp Val Arg Gly Asp Phe Cys Gly Cys
 1               5                  10

<210> SEQ ID NO 11
<211> LENGTH: 16
<212> TYPE: PRT
<213> ORGANISM: Artificial Sequence
<220> FEATURE:
<221> NAME/KEY: MOD_RES
<222> LOCATION: (2)
<223> OTHER INFORMATION: L-S-(3-aminopropyl)cysteine
<220> FEATURE:
<221> NAME/KEY: MOD_RES
<222> LOCATION: (6)
<223> OTHER INFORMATION: L-S-(3-aminopropyl)cysteine
<220> FEATURE:
<221> NAME/KEY: MOD_RES
<222> LOCATION: (11)
<223> OTHER INFORMATION: acetamidomethyl
<220> FEATURE:
<221> NAME/KEY: MOD_RES
```

-continued

```
<222> LOCATION: (13)
<223> OTHER INFORMATION: acetamidomethyl
<220> FEATURE:
<221> NAME/KEY: MOD_RES
<222> LOCATION: (16)
<223> OTHER INFORMATION: AMIDATION
<220> FEATURE:
<223> OTHER INFORMATION: Description of Artificial Sequence:synthetic
      peptide

<400> SEQUENCE: 11

Gly Xaa Gly Asp Val Xaa Gly Asp Phe Lys Cys Gly Cys Gly Gly Cys
 1               5                  10                  15

<210> SEQ ID NO 12
<211> LENGTH: 12
<212> TYPE: PRT
<213> ORGANISM: Artificial Sequence
<220> FEATURE:
<221> NAME/KEY: MOD_RES
<222> LOCATION: (2)
<223> OTHER INFORMATION: L-S-(3-aminopropyl)cysteine
<220> FEATURE:
<221> NAME/KEY: MOD_RES
<222> LOCATION: (7)
<223> OTHER INFORMATION: acetamidomethyl
<220> FEATURE:
<221> NAME/KEY: MOD_RES
<222> LOCATION: (9)
<223> OTHER INFORMATION: acetamidomethyl
<220> FEATURE:
<221> NAME/KEY: MOD_RES
<222> LOCATION: (12)
<223> OTHER INFORMATION: AMIDATION
<220> FEATURE:
<223> OTHER INFORMATION: Description of Artificial Sequence:synthetic
      peptide

<400> SEQUENCE: 12

Gly Xaa Gly Asp Val Lys Cys Gly Cys Gly Gly Cys
 1               5                  10

<210> SEQ ID NO 13
<211> LENGTH: 10
<212> TYPE: PRT
<213> ORGANISM: Artificial Sequence
<220> FEATURE:
<221> NAME/KEY: MOD_RES
<222> LOCATION: (2)
<223> OTHER INFORMATION: acetamidomethyl
<220> FEATURE:
<221> NAME/KEY: MOD_RES
<222> LOCATION: (4)
<223> OTHER INFORMATION: acetamidomethyl
<220> FEATURE:
<223> OTHER INFORMATION: Description of Artificial Sequence:synthetic
      peptide

<400> SEQUENCE: 13

Cys Cys Gly Cys Gly Gly Arg Gly Asp Ser
 1               5                  10

<210> SEQ ID NO 14
<211> LENGTH: 15
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (10)
<223> OTHER INFORMATION: acetamidomethyl
```

```
<220> FEATURE:
<221> NAME/KEY: MOD_RES
<222> LOCATION: (12)
<223> OTHER INFORMATION: acetamidomethyl
<220> FEATURE:
<221> NAME/KEY: MOD_RES
<222> LOCATION: (15)
<223> OTHER INFORMATION: AMIDATION
<220> FEATURE:
<223> OTHER INFORMATION: Description of Artificial Sequence:synthetic
      peptide

<400> SEQUENCE: 14

Arg Arg Ala Arg Gly Asp Asp Leu Asp Cys Gly Cys Gly Gly Cys
  1               5                  10                  15

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 15

Gly Arg Gly Asp Phe Gly Gly Cys
  1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 16

Gly Gly Arg Gly Asp Phe
  1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 17

Cys Gly Gly Gly Arg Gly Asp Phe
  1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 18

Gly Arg Gly Asp Gly Gly Cys
  1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence:synthetic
```

-continued peptide

<400> SEQUENCE: 19

Gly Gly Gly Arg Gly Asp Phe
  1               5

<210> SEQ ID NO 20
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: meercaptoacetyl
<220> FEATURE:
<223> OTHER INFORMATION: Description of Artificial Sequence:synthetic
      peptide

<400> SEQUENCE: 20

Arg Gly Asp Phe
  1

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 21

Gly Gly Arg Gly Asp Ser Cys
  1               5

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 22

Gly Gly Arg Gly Asp Gly Gly Arg Gly Asp Ser Cys
  1               5                  10

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 23

Gly Gly Arg Gly Asp Gly Gly Arg Gly Asp Gly Gly Arg Gly Asp Ser
  1               5                  10                  15

Cys

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 24

-continued

Arg Arg Arg Arg Arg Arg Arg Arg Arg Gly Asp Val Cys
 1               5                   10

<210> SEQ ID NO 25
<211> LENGTH: 7
<212> TYPE: PRT
<213> ORGANISM: Artificial Sequence
<220> FEATURE:
<221> NAME/KEY: MOD_RES
<222> LOCATION: (7)
<223> OTHER INFORMATION: AMIDATION
<220> FEATURE:
<223> OTHER INFORMATION: Description of Artificial Sequence:synthetic
      peptide

<400> SEQUENCE: 25

Cys Gly Arg Gly Asp Val Lys
 1               5

<210> SEQ ID NO 26
<211> LENGTH: 6
<212> TYPE: PRT
<213> ORGANISM: Artificial Sequence
<220> FEATURE:
<221> NAME/KEY: MOD_RES
<222> LOCATION: (6)
<223> OTHER INFORMATION: AMIDATION
<220> FEATURE:
<223> OTHER INFORMATION: Description of Artificial Sequence:synthetic
      peptide

<400> SEQUENCE: 26

Cys Gly Arg Gly Asp Val
 1               5

<210> SEQ ID NO 27
<211> LENGTH: 11
<212> TYPE: PRT
<213> ORGANISM: Artificial Sequence
<220> FEATURE:
<221> NAME/KEY: MOD_RES
<222> LOCATION: (11)
<223> OTHER INFORMATION: AMIDATION
<220> FEATURE:
<223> OTHER INFORMATION: Description of Artificial Sequence:synthetic
      peptide

<400> SEQUENCE: 27

Cys Gly Arg Gly Asp Val Arg Gly Asp Phe Lys
 1               5                   10

<210> SEQ ID NO 28
<211> LENGTH: 10
<212> TYPE: PRT
<213> ORGANISM: Artificial Sequence
<220> FEATURE:
<221> NAME/KEY: MOD_RES
<222> LOCATION: (10)
<223> OTHER INFORMATION: AMIDATION
<220> FEATURE:
<223> OTHER INFORMATION: Description of Artificial Sequence:synthetic
      peptide

<400> SEQUENCE: 28

Cys Gly Arg Gly Asp Val Arg Gly Asp Phe
 1               5                   10

<210> SEQ ID NO 29
<211> LENGTH: 13
<212> TYPE: PRT
<213> ORGANISM: Artificial Sequence -continued

```
<220> FEATURE:
<221> NAME/KEY: MOD_RES
<222> LOCATION: (2)
<223> OTHER INFORMATION: L-S-(3-aminopropyl)cysteine
<220> FEATURE:
<221> NAME/KEY: MOD_RES
<222> LOCATION: (6)
<223> OTHER INFORMATION: L-S-(3-aminopropyl)cysteine
<220> FEATURE:
<221> NAME/KEY: MOD_RES
<222> LOCATION: (13)
<223> OTHER INFORMATION: AMIDATION
<220> FEATURE:
<223> OTHER INFORMATION: Description of Artificial Sequence:synthetic
      peptide

<400> SEQUENCE: 29

Gly Xaa Gly Asp Val Xaa Gly Asp Phe Lys Gly Gly Cys
 1               5                  10

<210> SEQ ID NO 30
<211> LENGTH: 9
<212> TYPE: PRT
<213> ORGANISM: Artificial Sequence
<220> FEATURE:
<221> NAME/KEY: MOD_RES
<222> LOCATION: (2)
<223> OTHER INFORMATION: L-S-(3-aminopropyl)cysteine
<220> FEATURE:
<221> NAME/KEY: MOD_RES
<222> LOCATION: (9)
<223> OTHER INFORMATION: AMIDATION
<220> FEATURE:
<223> OTHER INFORMATION: Description of Artificial Sequence:synthetic
      peptide

<400> SEQUENCE: 30

Gly Xaa Gly Asp Val Lys Gly Gly Cys
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 31

Cys Gly Gly Arg Gly Asp Ser
 1               5

<210> SEQ ID NO 32
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (12)
<223> OTHER INFORMATION: AMIDATION
<220> FEATURE:
<223> OTHER INFORMATION: Description of Artificial Sequence:synthetic
      peptide

<400> SEQUENCE: 32

Arg Arg Ala Arg Gly Asp Asp Leu Asp Gly Gly Cys
 1               5                  10
```

```
<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 33

Cys Lys Arg Ala Arg Gly Asp Asp Met Asp Asp Tyr Cys
 1               5                  10

<210> SEQ ID NO 34
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (4)
<223> OTHER INFORMATION: AMIDATION
<220> FEATURE:
<223> OTHER INFORMATION: Description of Artificial Sequence:synthetic
      peptide

<400> SEQUENCE: 34

Arg Gly Asp Cys
 1

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 35

Cys Arg Gly Asp Cys
 1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 36

Gly Arg Gly Asp Gly Gly Gly Gly Cys
 1               5

<210> SEQ ID NO 37
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (4)
<223> OTHER INFORMATION: L-S-(3-aminopropyl)cysteine
<220> FEATURE:
<223> OTHER INFORMATION: Description of Artificial Sequence:synthetic
      peptide
```

```
<400> SEQUENCE: 37

Cys Asn Pro Xaa Gly Asp Cys
 1               5

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 38

Cys Arg Ile Ala Arg Gly Asp Trp Asn Asp Asp Tyr Cys
 1               5                  10

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 39

Cys Lys Phe Phe Ala Arg Thr Val Cys Arg Ile Ala Arg Gly Asp Trp
 1               5                  10                  15

Asn Asp Asp Tyr Cys Thr Gly Lys Ser Ser Asp Cys
            20                  25

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 40

Lys Tyr Gly Gly His His Leu Gly Gly Ala Lys Gln Ala Gly Asp Val
 1               5                  10                  15
```

THROMBOLYTIC AGENTS WITH ANTITHROMBOTIC ACTIVITY

This invention was made with government support under R41 HL52995 by the National Institutes of Health. The government has certain rights in the invention.

BACKGROUND OF THE INVENTION

1. Field of the Invention

This invention relates to thrombolytic agents and methods for making and using thrombolytic agents. Specifically, the invention relates to thrombolytic agents comprising a thrombolytic proteinase and a specific binding peptide that specifically binds at the site of blood clots and thrombi in vivo. The invention particularly provides chemically crosslinked conjugates of a thrombolytic proteinase and a plurality of specific binding peptides. Methods for producing such chemically crosslinked conjugates and methods for using such conjugates for eliminating thrombi in vivo to alleviate pathological conditions caused thereby are also provided by the invention.

2. Description of the Related Art

Thrombosis and thromboembolism, the occurrence of occlusive thrombi in the vasculature of human patients, poses a significant clinical problem and is a significant cause of morbidity and mortality. Arterial thrombi are responsible for myocardial infarction (MI) and ischemia (stroke), while venous thrombi cause deep vein thrombosis (DVT) and pulmonary embolism (PE). The magnitude of the clinical challenge created by thrombi is reflected in morbidity and mortality statistics. One of the leading causes of death in men over the age of 50 is acute MI, and stroke remains a debilitating and unpredictable disease. It has been estimated that in the U.S. approximately 5 million patients experience one or more episodes of DVT per year and that over 500,000 cases of PE occur, resulting in 100,000 deaths (Seabold, Society of Nuclear Medicine Annual Meeting 1990).

Anticoagulant therapy can effectively treat these conditions in many cases, if applied early enough. However, such treatment is associated with risks (e.g. internal bleeding) that preclude unnecessary prophylactic application. More advanced techniques of thrombolytic intervention (such as the administration of recombinant tissue plasminogen activator or streptokinase) can be used in acute cases, but these techniques carry even greater risks, due in large part to systemic side effects. In addition, particularly in arterial thrombi, rethrombosis and reocclusion of blood vessels at the thrombus site is a significant (10–30%) clinical outcome. Even using these advanced methodologies, 25–30% of acute MI patients fail to restore perfusion to the thrombus-occluded coronary artery that are the proximal cause of the heart attack.

Thrombi are comprised of blood cells, largely platelets, enmeshed in cross-linked fibrin protein. Thrombus formation involves the conversion of fibrinogen to fibrin and the physiological conversion of unactivated platelets to an activated state. Little fibrin circulates in the bloodstream (in contrast to its precursor, fibrinogen) and most circulating platelets are unactivated, so that fibrin and activated platelets are specifically located at thrombus sites and comprise specific targets for agents designed to dissolve and eliminate thrombi.

Existing pharmaceutical agents for attacking and dissolving thrombi are directed towards enzymatic digestion of the fibrin matrix. Thus, streptokinase, urokinase and tissue plasminogen activator (tPA) are currently in clinical use for dissolving arterial thrombi, particularly arterial thrombi found in cardiac blood vessels. However, the systemic side effects of these agents (systemic fibrinogenolysis and bleeding) raise significant clinical difficulties. These side effects are the result, at least in part, of the fact that these therapeutic agents comprise proteolytic components of the blood clotting cascade, and thus their thrombolytic capabilities are also responsible for their capacity to disrupt hemostasis systemically, particularly at dosages required to result in therapeutically effective delivery of these drugs to the thrombus site. Thus, the outcome of clinical administration of these agents would be improved if a thrombolytic agent was specifically targeted to thrombus sites in vivo, thereby reducing the incidence of unwanted systemic side effects.

Pharmaceutical agents directed towards achieving targeted delivery of thrombolytic agents to thrombus sites in vivo have been reported in the prior art.

Bajwa et al., 1980, Toxicon 18: 285–290 disclose the existence of fibrinolytic enzyme activity in snake venom.

Gartner et al., 1985, J. Biol. Chem. 260: 11891–11894 disclose RGD analogues for inhibiting platelet aggregation and fibrinogen binding.

Plow et al., 1987, Biochem. Pharmacol. 36: 4036–4040 provide a review of platelet-fibrinogen interactions related to thrombus formation.

Bode et al., 1987, J. Biol. Chem. 262: 10819–10823 disclose an antibody-urokinase conjugate for targeting to fibrin.

Retzios et al., 1988, Thromb. Res. 52: 541–552 disclose biochemical characterization of fibrolase.

Dewerchin et al., 1989, Eur. J. Biochem. 185: 141–149 disclose urokinase-antifibrin$_{XL}$ monoclonal antibody conjugates.

Coller et al., 1989, Circulat. 80: 1766–1774 disclose monoclonal antibodies to platelet GPIIb/IIIa receptors for abolishing thrombus formation in vivo.

Shebuski et al., 1989, Thrombos. Haemostas. 61: 183–188 disclose the use of RGDS peptides as antiaggregatory agents in vivo.

Dennis et al., 1989, Proc. Natl. Acad. Sci. USA 87: 2471–2475 disclose the existence of a class of platelet GPIIb/IIIa antagonists in snake venom.

Shebuski et al., 1990, Circulat. 82: 169–177 disclose the combination of heparin, bitistatin and tissue plasminogen activator as an improved embodiment of a thrombolytic regimen.

Ahmed et al., 1990, Haemostasis 20: 334–340 disclose the thrombolytic properties of fibrolase isoform A.

Charpie et al., 1990, Biochem. 29: 6374–6378 disclose bispecific monoclonal antibody-derived hybrids directed towards fibrin and urokinase.

Runge et al., 1990, Bioconj. Chem. 1: 274–277 disclose bispecific monoclonal antibody-derived hybrids directed towards fibrin and plasminogen activator.

Collen, 1990, Ann. Intern. Med. 112: 529–538 provide a comparison of the benefits of treating myocardial infarction with streptokinase and tissue plasminogen activator.

Rapaport, 1991, Amer. J. Cardiol. 68: 17E–22E provides a review of the use of thrombolytic agents for treatment of thrombi in vascular disease.

Yasuda et al., 1991, Circulat. 83: 1038–1047 disclose a polypeptide platelet GPIIb/IIIa antagonist.

Holahan et al., 1991, Pharmacol. 42: 340–348 disclose the use of echistatin to prevent reocclusion following tissue plasminogen activator thrombolysis.

Dewerchin et al., 1991, *Blood* 78: 1005–1018 disclose plasminogen activator-antibody conjugates.

Branscomb et al., 1991, *Thromb. Haemostas.* 64: 260–266 disclose bispecific monoclonal antibody-derived hybrids directed towards fibrin and urokinase.

Runge et al., 1991, *Proc. Natl. Acad. Sci. USA* 88: 10337–10341 disclose conjugates between an anti-fibrin monoclonal antibody and tissue plasminogen activator.

Kurokawa et al., 1991, *Thromb. Haemostas.* 66: 684–693 disclose bispecific monoclonal antibody-derived hybrids directed towards fibrin and urokinase.

Guan et al., 1991, *Arch. Biochem. Biophys.* 289: 197–207 disclose purification and characterization of fibrolase from snake venom.

D'Souza et al., 1991, *Trends in Biochem. Sci.* 16: 246–250 provide a review of RGD peptides and their role in cell adhesion and thrombus formation.

Abel, 1992, *Acta Cardiol.* 47: 287–295 provide a review of thrombolysis as a general approach to treating vascular occlusion.

Haber et al., 1992,. *Ann. N.Y. Acad Sci.* 667: 365–381 disclose the use of antibody targeting as a thrombolytic strategy.

Randolph et al., 1992, *Protein Science* 1: 590–600 disclose the amino acid sequence of fibrolase.

Neblock, 1992, *Bioconj. Chem.* 3: 126–131 disclose conjugates between a platelet-specific antibody and tissue plasminogen activator.

Baker et al., 1992, *J. Med. Chem.* 35: 2040–2048 disclose cyclic RGD peptides as antithrombotic agent.

Du et al., 1993, *Sci. China B* 36: 1483–1489 disclose a urokinase conjugate to an antibody specific for activated human platelets.

More et al., 1993, *Cardiovasc. Res.* 27: 2200–2204 disclose conjugates between urokinase and monoclonal antibodies specific for platelet GPIIb/IIIa receptor and damaged endothelium.

Holvoet et al., 1993, *Blood* 81: 696–703 disclose a conjugate between a fibrin-specific single chain Fv antibody fragment and single-chain urokinase.

Markland et al., 1994, *Circulat.* 90: 2448–2456 disclose the thrombolytic effects of recombinant fibrolase.

Trika et al., 1994, *Thromb. Res.* 73: 39–52 disclose purification of platelet GPIIb/IIIa antagonists from snake venom.

Trika et al., 1994, *Toxicon* 32: 1521–1531 disclose purification of different isoforms of fibrolase to snake venom.

Phaneuf et al., 1994, *Thromb. Haemostas.* 71: 481–487 disclose streptokinase-hirudin conjugates for thrombolytic targeting.

Bode et al., 1994, *Ann. Hematol.* 69: S35–S40 provide a general review of thrombolytic approaches to treating myocardial infarction.

In addition to their thrombolytic activity, the thrombolytic agents in current clinical use can also activate thrombin and plasmin at the thrombus site, increasing the likelihood of the re-formation of the thrombus and reocclusion of the vessel. Interaction between platelets and fibrinogen constitutes a critical step in reocclusion, comprising the seeding point for the re-formation of the thrombus. Disruption of the interaction of platelets and fibrinogen would therefore comprise an effective inhibitor to thrombus re-formation.

The interaction between platelets and fibrinogen has been recognized to reside in the platelet glycoprotein IIb/IIIa integrin receptor, which recognizes the amino acid motif -Arg-Gly-Asp found in the fibrinogen protein. This motif therefore comprises a means for specific, targeted disruption of the platelet-fibrinogen interaction.

Peptides and other compounds capable of binding to platelets via the GPIIb/IIIa receptor are known in the prior art.

Ruoslahti & Pierschbacher, U.S. Pat. No. 4,578,079 describe peptides of sequence X-Arg-Gly-Asp-R-Y, wherein X and Y are either H or an amino acid, and R is Thr or Cys, the peptides capable of binding to thrombi in vivo.

Ruoslahti & Pierschbacher, U.S. Pat. No. 4,792,525 describe peptides of sequence Arg-Gly-Asp-X, wherein X is Ser, Thr or Cys, the peptides capable of binding to thrombi in vivo.

Klein et al., 1992, U.S. Pat. No. 5,086,069 disclose guanine derivatives that bind to the GPIIb/IIIa receptor as found on the cell surface of activated platelets.

Pierschbacher et al., 1989, PCT/US88/04403 disclose conformationally-restricted RGD-containing peptides for inhibiting cell attachment to a substratum.

Hawiger et al., 1989, PCT/US89/01742 relates to peptides comprising sequences for two binding sites of a protein.

Nutt et al., 1990, European Patent Application 90202015.5 disclose cyclic RGD peptides that are fibrinogen receptor antagonists.

Nutt et al., 1990, European Patent Application 90202030.4 disclose cyclic RGD peptides that are fibrinogen receptor antagonists.

Nutt et al., 1990, European Patent Application 90202031.2 disclose cyclic RGD peptides that are fibrinogen receptor antagonists.

Nutt et al., 1990, European Patent Application 90202032.0 disclose cyclic RGD peptides that are fibrinogen receptor antagonists.

Nutt et al., 1990, European Patent Application 90311148.2 disclose cyclic peptides that are fibrinogen receptor antagonists.

Nutt et al., 1990, European Patent Application 90311151.6 disclose cyclic peptides that are fibrinogen receptor antagonists.

Ali et al., 1990, European Patent Application 90311537.6 disclose cyclic peptides that are fibrinogen receptor antagonists.

Barker et al., 1991, PCT/US90/03788 disclose cyclic peptides for inhibiting platelet aggregation.

Pierschbacher et al., 1991, PCT/US91/02356 disclose cyclic peptides that are fibrinogen receptor antagonists.

Egbertson et al., 1992, European Patent Application 0478328A1 disclose tyrosine derivatives that bind with high affinity to the GPIIb/IIIa receptor.

Ojima et al., 1992, 204th Meeting, Amer. Chem. Soc. Abst. 44 disclose synthetic multimeric RGDF peptides useful in inhibiting platelet aggregation.

Hartman et al., 1992, *J Med. Chem.* 35: 4640–4642 describe tyrosine derivatives that have a high affinity for the GPIIb/IIIa receptor.

International Patent Application Nos. PCT/US93/04794, PCT/US94/03878 and PCT/US95/06909 to Diatide disclose GPIIb/IIIa binding specific binding peptides.

Thus, there remains a need in the art to target thrombolytic agents specifically to thrombus sites in vivo and thereby reduce or eliminate deleterious systemic side effects resulting from the administration of these agents. There also remains a need to inhibit re-formation of thrombi and re-occlusion of blood vessels with such thrombi after acute resolution of a thrombotic episode, especially in instances of MI. There remains a need for the development of agents capable of fulfilling both roles as specifically-targeted thrombolytic agents and platelet aggregation/fibrinogen interaction antagonists. Chemically crosslinked conjugates of thrombolytic agents and specific binding peptides, and in particular platelet binding peptides, fulfill this need and are provided by this invention as disclosed herein.

SUMMARY OF THE INVENTION

The present invention provides thrombolytic agents that are specifically targeted to thrombus sites in vivo. The invention provides such agents as conjugates between a proteolytic enzyme and a specific binding peptide that specifically binds at the thrombus site. Conjugation of these components is preferably mediated by a chemical crosslinking agent.

The invention provides a thrombolytic agent comprising a homogeneous preparation of a thrombolytic proteinase that is chemically cross-linked to a linear or cyclic specific binding peptide that specifically binds to a thrombus site in vivo. In a preferred embodiment, the specific binding peptide specifically binds to platelets and is capable of inhibiting platelet aggregation and inhibiting platelet-fibrinogen interactions. In another preferred embodiment, the specific binding peptide specifically binds to fibrin. In a preferred embodiment, the thrombolytic proteinase is an isoform of fibrolase. In a particularly preferred embodiment, the fibrolase is isolated from *Agkistrodon contortrix contortrix* venom and identified as EC 3.4.24.72. In an additional preferred embodiment, *Agkistrodon contortrix contortrix* fibrolase is prepared using recombinant genetic techniques.

In other preferred embodiments of the thrombolytic conjugates of the invention, the specific binding peptide specifically binds to the platelet GPIIb/IIIa receptor. In preferred embodiments, the specific binding peptide has an amino acid sequence comprising the sequence -XGD-, wherein X is any amino acid having a sidechain comprising an amino group, a guanidino group or an amidino group. In preferred embodiments, the peptide comprises from about 4 to about 99 amino acids, more preferably about 4 to about 50 amino acids, and most preferably from about 4 to about 20 amino acids in the amino acid sequence comprising the sequence -XGD-.

In other preferred embodiments, the specific binding peptide comprises an amino acid sequence of 4 to 100 amino acids wherein the peptide is selected from the group consisting of linear and cyclic peptides that are ligands for a GPIIb/IIIa receptor and peptides that are ligands for a polymerization site of fibrin.

In another preferred embodiment, the specific binding peptides that are ligands for the GPIIb/IIIa receptor comprise the amino acid sequence (-His-His-Leu-Gly-Gly-Ala-Lys-Gln-Ala-Gly-Asp-Val-) (SEQ ID NO:1).

In another preferred embodiment, the specific binding peptides that are ligands for a polymerization site of fibrin comprise multiple copies of the amino acid sequence (glycyl-prolyl-arginyl-prolyl) (SEQ ID NO:2).

The thrombolytic conjugates of the invention also comprise a chemical conjugating moiety that mediates conjugation between the specific binding peptide and the thrombolytic proteinase. In preferred embodiments, the chemical conjugating moiety is a heterobifunctional crosslinking agent. Preferred embodiments of such agents include N-succinimidyl-2-(2-pyridyldithio) propionate, N-(γ-maleimidobutyryloxy) sulfosuccinimide ester or sulfosuccinimidyl-6-(α-methyl-α-(2-pyridyldithio) toluamido)hexonate. In additional preferred embodiments, the thrombolytic proteinase is conjugated with from about 1 to about 10, more preferably from about 1 to about 5 and most preferably from about 1 to about 3 copies of the specific binding peptide.

In preferred embodiments, the thrombolytic conjugates of the invention are provided having an $IC_{50}$ for inhibiting platelet aggregation of not greater than 1 μM, more preferably not greater than 0.3 μM and most preferably not greater than 0.1 μM.

Also provided by the invention are radioactively-labeled embodiments wherein the conjugates of the invention are labeled with a radioisotope, most preferably a gamma radiation-emitting radioisotope.

The invention also provides methods for producing the conjugates of the invention as described in detail herein.

This invention provides methods for using the thrombolytic agents of the invention for dissolving clots at pathological sites in vivo, which agents specifically target the site of the blood clot. These methods comprise administering an effective therapeutic amount of thrombolytic agents of the invention.

The invention also provides methods whereby targeting and dissolution of the blood clot can be monitored by gamma scintigraphy. These methods comprise administering an effective therapeutic amount of thrombolytic agents of the invention comprising a radiolabeled portion thereof, detecting radiation, preferably gamma radiation emitted by the radiolabel localized at the thrombus site within the mammalian body, and observing diminution of the signal as the thrombus is dissolved by the thrombolytic agent.

The thrombolytic agents of the invention possess several advantages over thrombolytic agents known in the prior art. First, the thrombolytic agents of the invention are specifically targeted to thrombosis sites in vivo, due to conjugation with specific binding peptides that specifically bind to thrombi, in particular fibrin and platelets which comprise the thrombus and hence are found at the thrombus site. As a result, the thrombolytic agents of the invention display less systemic side effects that other thrombolytic compounds, such as streptokinase and tissue plasminogen activator, because the proteolytic activity is localized at the thrombus site. This feature of the thrombolytic agents of the invention also provides increased therapeutic dosage levels at the site of the thrombus, because the specific binding peptide increases the affinity of the agent specifically for the thrombus site. Thus, a lower amount of the thrombolytic agent may be administered to achieve a therapeutic threshold, thereby further decreasing the systemically administered dosage of the thrombolytic agent. Second, the preferred proteinase component of the thrombolytic agents of the invention, fibrolase, has a direct fibrinolytic activity that is not a part of the plasminogen/plasmin proteolytic cascade, and so does not activate re-thrombosis by recruitment of thrombin and other proteolytic components of the blood clotting system. Also, the preferred embodiment is a metalloproteinase rather than a serine protease, and thus is not inhibited by serpins and other circulating inhibitors of serine protease activity found in animal circulation. Third, in the particularly preferred embodiment, fibrolase isolated from the southern copperhead snake (*Agkistrodon contortrix contortrix*) has no intrinsic hemorrhagic capacity, as is known with other snake venoms, so that administration of fibrolase-containing thrombolytic agents is not associated with iatrogenic hemostatic complications. Fourth, the thrombolytic agents of the invention can be specifically radiolabeled, most preferably with a gamma-emitting radioisotope, and the localization and therapeutic course of thrombus dissolution can thereby be monitored.

Specific preferred embodiments of the present invention will become evident from the following more detailed description of certain preferred embodiments and the claims.

BRIEF DESCRIPTION OF THE DRAWINGS

FIG. 3 illustrates the reaction scheme for the conjugation of fibrolase with a specific binding peptide of the invention using N-succinimidyl-3-(2-pyridyldithio) propionate (SPDP).

FIG. 5 shows the results of HPLC purification of SPDP crosslinked fibrolase:peptide conjugates. Panel A illustrates the elution profile of unconjugated fibrolase isoform 2 control; Panel B shows the elution profile of unconjugated peptide; Panel C shows the elution profile of SPDP-linked fibrolase; and Panel D shows the elution profile of fibrolase:peptide conjugates crosslinked with SPDP.

DETAILED DESCRIPTION OF THE PREFERRED EMBODIMENTS

Figure 1:
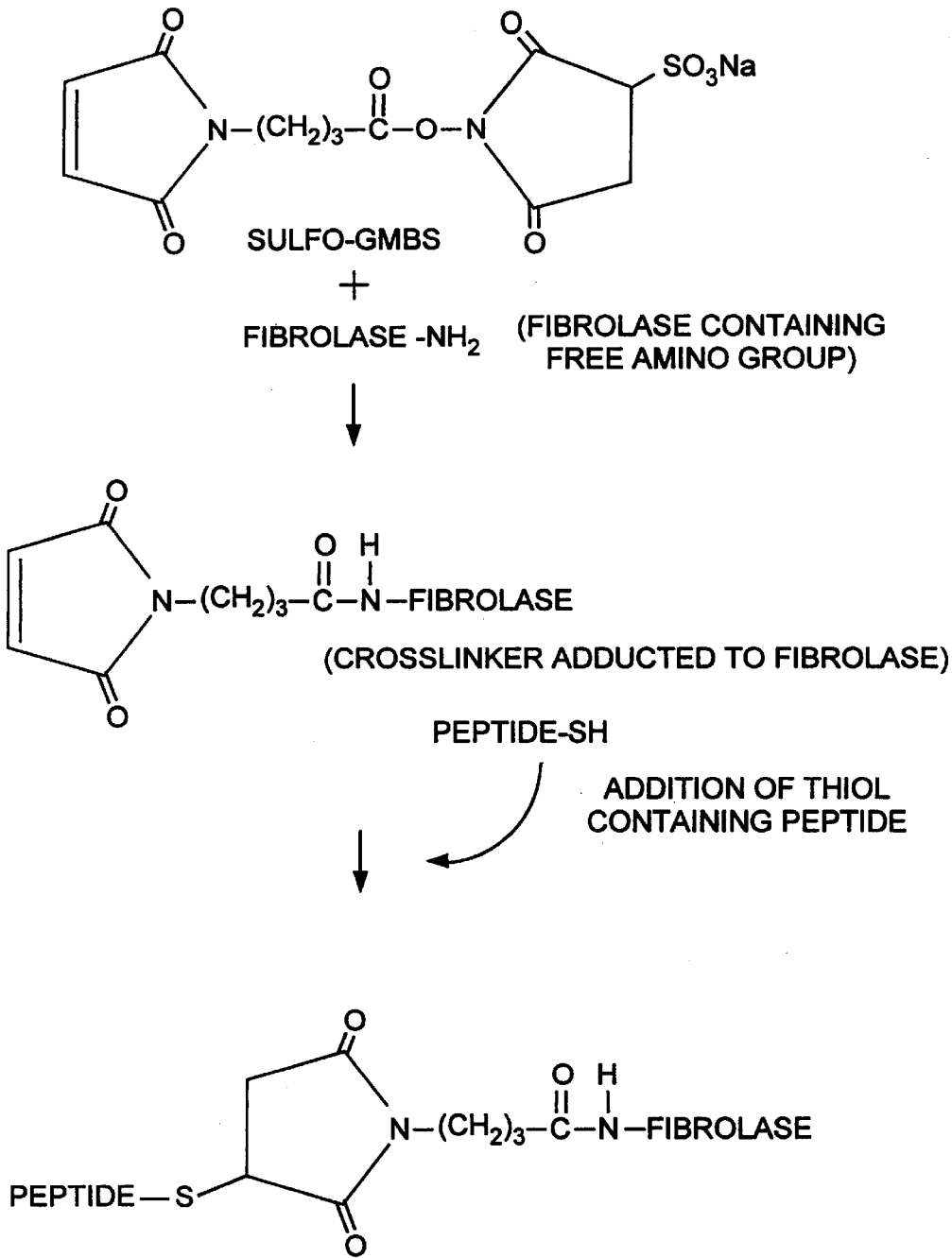
FIG. 1 illustrates the reaction scheme for the conjugation of fibrolase with a specific binding peptide of the invention using N-(γ-maleimidobutyryloxy) sulfosuccinimide ester (S-GMBS).

The present invention provides thrombolytic agents comprising a thrombolytic proteinase and a specific binding peptide that binds to thrombi, and in particular, fibrin and platelets in vivo, and that specifically targets the thrombolytic agent to thrombus sites.

For the purposes of this invention, the term "thrombolytic agent" will be understood to encompass any enzymatic or chemical agent that disrupts, dissolves, digests, dissociates, lyses, reduces, eliminates or ameliorates (collectively termed "thrombolytic properties") thrombi and blood clots in arteries, veins, arterioles, capillaries and other vascular structures in an animal body, as well as in various tissue sites including but not limited to brain, lung, kidney, skin, heart, and deep veins of the leg.

For the purposes of this invention, the term "thrombolytic proteinase" is intended to encompass naturally-occurring and man-made compounds having a catalytic activity that disrupts, dissolves, digests, dissociates, lyses, reduces, eliminates or ameliorates the proteinaceous components of thrombi and blood clots, including but not limited to fibrin and fibrinogen. Exemplary thrombolytic proteinases include plasmin and plasminogen, urokinase, streptokinase, and most preferably, fibrolase, including fragments thereof having proteolytic activity. The invention is intended to encompass any embodiment of an enzymatic or catalytic activity having the thrombolytic properties described herein. Specifically encompassed by the invention is recombinant fibrolase, prepared using recombinant genetic technology as disclosed in European Patent Application No. 323722 and Loayza et al. (Ibid.).

For the purposes of this invention, the term "specific binding peptide" is intended to encompass peptides (defined as comprising from 3 to 100 amino acids) having a biological affinity for specific components of tissues and other biological structures, including most preferably fibrin and platelets. The specific binding peptides of the invention are preferably provided as having specificity for and targeting capacity to platelets, particularly platelets comprising thrombi, and fibrin, and that facilitate the specific localization to thrombus sites in vivo. Examples of such specific binding peptides useful as components of the thrombolytic agents of the invention include peptides comprising the amino acid sequence -XGD-, wherein X is an amino acid comprising an amino group, a guanidino group or an amidino group in its sidechain, -GPRP- (SEQ ID NO:2), or a peptide comprising the sequence -HHLGGAKQAGDV- (SEQ ID NO: 1), and including but not limited to peptides having the following formulae:

CH$_2$CO.Y$_D$.Apc.GDCGGC$_{Acm}$GC$_{Acm}$GGC.amide,
CH$_2$CO.Y$_D$.Apc.GDCKGC$_{Acm}$GC$_{Acm}$GGC.amide,
C$_{Acm}$GC$_{Acm}$GGRGDSC (SEQ ID NO: 3),
C$_{Acm}$GC$_{Acm}$GGRGDGGRGDSC (SEQ ID NO: 4),
C$_{Acm}$GC$_{Acm}$GGRGDGGRGDGGRGDSC (SEQ ID NO: 5),
C$_{Acm}$GC$_{Acm}$RRRRRRRRRGDVC (SEQ ID NO: 6),
CGRGDVKC$_{Acm}$GC$_{Acm}$.amide (SEQ ID NO: 7),
CGRGDVC$_{Acm}$GC$_{Acm}$.amide (SEQ ID NO: 8),
CGRGDVRGDFKC$_{Acm}$GC$_{Acm}$.amide (SEQ ID NO: 9),
CGRGDVRGDFC$_{Acm}$GC$_{Acm}$.amide (SEQ ID NO: 10),
acetyl-G.Apc.GDV.Apc.GDFKC$_{Acm}$GC$_{Acm}$.GGCamide (SEQ ID NO: 11),
G.Apc.GDV.Apc.GDFKC$_{Acm}$GC$_{Acm}$.GGCamide (SEQ ID NO: 11),
G.Apc.GDVKC$_{Acm}$GC$_{Acm}$GGC.amide (SEQ ID NO: 12),
CC$_{Acm}$GC$_{Acm}$GGRGDS (SEQ ID NO: 13),
acetyl-RRARGDDLDC$_{Acm}$GC$_{Acm}$.GGC.amide (SEQ ID NO: 14),
GRGDFGGC$_{Acm}$ (SEQ ID NO: 15),
ma$_{Bz}$-GGRGDF (SEQ ID NO: 16),
C$_{Acm}$GGGRGDF (SEQ ID NO: 17),
GRGDGGC$_{Acm}$ (SEQ ID NO: 18),
ma-GGRGDF (SEQ ID NO: 16),
ma$_{Acm}$-GGGRGDF (SEQ ID NO: 19),
ma-RGDF (SEQ ID NO: 20),
ma-RGD,
CH$_2$CO.Y$_D$.Apc.GDCGGC.amide,
CH$_2$CO.Y$_D$.Apc.GDCGGGC.amide,
CH$_2$CO.Y$_D$.Apc.GDCKGGC.amide,
CH$_2$CO.Y$_D$.Apc.GDCGGGC.amide,
GGRGDSC (SEQ ID NO: 21),
GGRGDGGRGDSC (SEQ ID NO: 22),
GGRGDGGRGDGGRGDSC (SEQ ID NO: 23),
RRRRRRRRRGDVC (SEQ ID NO: 24),
CGRGDVK.amide (SEQ ID NO: 25),
CGRGDV.amide (SEQ ID NO: 26),
CGRGDVRGDFK.amide (SEQ ID NO: 27),
CGRGDVRGDF.amide (SEQ ID NO: 28),
acetyl-G.Apc.GDV.Apc.GDFKGGCamide (SEQ ID NO: 29),
G.Apc.GDV.Apc.GDFKGGCamide (SEQ ID NO: 29),
G.Apc.GDVKGGC.amide (SEQ ID NO: 30), CGGRGDS (SEQ ID NO: 31),
acetyl-RRARGDDLDGGC.amide (SEQ ID NO: 32),
CKRARGDDMDDYC (SEQ ID NO: 33),
mmp-GGGRGDF (SEQ ID NO: 19),
acetyl-RGDC.amide (SEQ ID NO: 34),
CRGDC (SEQ ID NO: 35),
CGGGRGDF (SEQ ID NO: 17),
GRGDGGGGC (SEQ ID NO: 36),
GRGDGGC (SEQ ID NO: 18),
ma$_{Acm}$-GGGRGDF (SEQ ID NO: 19),
acetyl-CNP.Apc.GDC (SEQ ID NO: 37),
CRIARGDWNDDYC (SEQ ID NO: 38),
CKFFARTVCRIARGDWNDDYCTGKSSDC (SEQ ID NO: 39),
KYGGHHLGGAKQAGDV (SEQ ID NO: 40),
(CH$_2$CO-Y$_D$.Amp.GDCKGCG.amide)$_2$-(ε-K)GC.amide, or
CH$_2$CO-Y$_D$.Amp.GDCKGCG.amide.

Each specific-binding peptide-containing embodiment of the invention is comprised of a sequence of amino acids. The term amino acid as used in this invention is intended to include all L- and D-amino acids, naturally occurring and otherwise. Single-letter abbreviations for amino acids can be found in Zubay, Biochemistry (2d. ed.), 1988 (MacMillen Publishing: New York) p.33; underlining indicates the formation of a thiol linkage between the linked amino acids or derivative groups; Ac=acetyl; Bz=benzoyl; Amp=4-amidinophenylalanine; (ε-K)=lysine linked through the sidechain (epsilon) amino group; Acm=acetamidomethyl; Mob=4-methoxybenzyl; Apc=L-S-(3-aminopropyl) cysteine; Hly=homolysine; F$_D$=D-phenylalanine; Y$_D$=D-tyrosine; ma=2-mercaptoacetic acid; mmp=2-mercapto-2-methylpropionic acid. This list of specific binding peptides provided by the invention is illustrative and not intended to be limiting or exclusive, and it will be understood by those with skill in the art that peptides comprising combinations of the peptides disclosed herein or their equivalents may be covalently linked to any of the thrombolytic proteinases of the invention and be within its scope.

In preferred embodiments of the invention comprising peptides having an amino acid sequence that binds to the platelet GPIIb/IIIa receptor, each said specific binding peptide is capable of inhibiting human platelet aggregation in platelet-rich plasma by 50% when present at a concentration of no more than 1 mM, more preferably no more than 0.3 μM, and most preferably no more than 0.1 mM.

Specific-binding peptides of the present invention can be chemically synthesized in vitro. Peptides of the present invention can generally advantageously be prepared on an amino acid synthesizer.

The specific binding peptides of the invention and the thrombolytic proteinase are covalently linked in the thrombolytic agents of the invention by a chemical conjugating moiety. In preferred embodiments, this moiety comprises a heterobifunctional chemical conjugating moiety. Preferred embodiments of the chemical conjugating moieties comprising the thrombolytic agents of the invention include but are not limited to N-succinimidyl-2-(2-pyridyldithio) propionate, N-(γ-maleimidobutyryloxy) sulfosuccinimide ester, succinimidyl 4-(p-maleimidophenyl)butyrate, sulfosuccinimidyl-4-(p-maleimidophenyl)butyrate, 4-succinimidyloxycarbonyl-methyl-α-(2-pyridyldithio) toluene, N-hydroxysuccinimidyl-2,3-dibromopropionate, N-succinimidyl-(4-iodoacetyl)-aminobenzoate, sulfosuccinimidyl-(4-iodoacetyl)-aminobenzoate, succinimidyl-4-(N-maleimidomethyl)cyclohexane-1-carboxylate, sulfosuccinimidyl-4-(N-maleimidomethyl)cyclohexane-1-carboxylate, N-(γ-maleimidobutyryloxy) succinimide ester, m-maleimidobenzenyl-N-hydroxysuccinimide ester, m-maleimidobenzenyl-N-hydroxysulfosuccinimide ester, sulfosuccinimidyloxycarbonyl-6-(α-methyl)-α-(2-pyridyldithio) toluamide hexanoate, and sulfosuccinimidyl-6-(α-methyl-α-(2-pyridyldithio)toluamido)hexanoate.

In certain embodiments of the thrombolytic agents of this invention, the agent is radiolabeled, preferably with a gamma-emitting radioisotope such as Tc-99m, $^{111}$In, $^{68}$Ga, $^{125}$I or $^{131}$I (see, for example, Pearson et al., 1996, J. Med. Chem. 39: 1372–1382). Radioactively-labeled thrombolytic agents provided by the present invention are provided having a suitable amount of radioactivity. Generally, the dose of radiolabeled thrombolytic agent administered has a radioactivity of about 0.01 mCi to about 100 mCi, preferably 1 mCi to 20 mCi.

An advantageous feature of the thrombolytic agents of the invention is that localization of such agents can be visualized, and the course of thrombolysis can be monitored, in vivo, and in real time. Administration of radiolabeled thrombolytic agents can therefore be used to closely monitor course of treatment and facilitate choice and administration of therapeutically effective amounts of the thrombolytic agents of the invention.

The thrombolytic agents provided by the present invention are usefully provided as pharmaceuticals for lysing thrombi in vivo. In accordance with the teachings of this invention, the inventive thrombolytic agents are administered in a single unit injectable dose. These agents can be administered intravenously in any conventional medium for intravenous injection such as an aqueous saline medium, or in blood plasma medium. The solution to be injected at unit dosage is from about 0.01 mL to about 10 mL. The thrombolytic agents of the invention are preferably administered at a dose of from about 0.1 to about 10 mg/kg body weight, administered intravenously either totally as a bolus or partly as a bolus followed by infusion over 1–2 hours. In radiolabeled embodiments of the thrombolytic agents, the unit dose to be administered has a radioactivity of about 0.01 mCi to about 100 mCi, preferably 1 mCi to 20 mCi. After intravenous administration, the thrombus site is monitored, in certain embodiments by radioimaging in vivo.

The methods for making, radiolabeling and using the thrombolytic agents of the invention are more fully illustrated in the following Examples. These Examples illustrate certain aspects of the above-described method and advantageous results. These Examples are shown by way of illustration and not by way of limitation.

EXAMPLE 1

Purification of Fibrolase

Fibrolase was purified from Agkistrodon contortrix contortrix venom using a biochemical purification protocol as disclosed in Loayza et al. (1994, J. Chromatog. B 662: 227–243).

Briefly, crude snake venom was obtained from Biotoxins, Inc. (St. Cloud, Fla.) or from the Miami Serpentarium Laboratory (Punta Gorda, Fla.). All purification steps were performed at 4° C. Ten grams of venom were applied in five applications to a 100 mm hydrophobic interaction chromatography column (HIC; Poly Propyl A, Poly LC, Western Analytical Products, Temecula, Calif.) having a 21 mm internal diameter. Venom was dissolved at a concentration of 2 g per 9 mL HIC buffer A (comprising 0.1M phosphate, 1M ammonium sulfate, and 0.02% sodium azide, pH 6.8) and subjected to centrifugation at 9000 g for 30 min at 4° C. to remove particulate contaminants. The resulting supernatant solution was filtered though a 0.2 µm membrane and then applied to the HIC column. Venom proteins were eluted from the column using a gradient elution protocol as follows: (a) 50 min isocratically at 100% HIC buffer A; (b) 90 min using a linear gradient to 100% HIC buffer B (comprising 0.1M phosphate and 0.02% sodium azide, pH 6.8); and (c) 60 min isocratically at 100% HIC buffer B. Flow rate through the column was maintained at 5 mL/min, and 5 mL fractions were collected. Fractions were monitored spectrophotometrically using absorbance at 280 nm, and analyzed for fibrinolytic activity, and by sodium dodecyl sulfate-polyacrylamide gel electrophoresis (SDS-PAGE).

Fractions containing fibrinolytic activity were pooled, concentrated using 80% ammonium sulfate, and dialyzed against hydroxyapatite (HAP) buffer (comprising 0.01M phosphate, 0.02% sodium azide, pH 6.8). This dialyzed sample was concentrated using either a stirred cell containing a YM 10 membrane or a Centricon-10 concentrator (both obtained from Amicon, Beverly, Mass.) to a final volume of about 10 mL.

This concentrated sample was then applied to a 100 mm hydroxyapatite (HAP) column (SynChropak HAP-5, SynChrom, Lafayette, Ind.) having a 21.1 mm internal diameter. Venom proteins were eluted from this column using a gradient elution protocol as follows: (a) 15 min isocratically at 100% HAP buffer A; (b) 130 min using a linear gradient to 60% HAP buffer B (comprising 0.35M phosphate and 0.02% sodium azide, pH 6.8); and (c) 35 min linear gradient to 100% HAP buffer B. Flow rate through the column was maintained at 2 mL/min, and 2 mL fractions were collected. As above, fractions were monitored spectrophotometrically using absorbance at 280 nm, and analyzed for fibrinolytic activity and by SDS-PAGE.

Anion-exchange chromatography using a 100 mm high resolution fast protein liquid chromatography column (Mono Q, Pharmacia LKB, Piscataway, N.J.) having an internal diameter of 16 mm column was used for removal of minor contaminants from fractions containing fibrinolytic activity. HAP chromatography fractions having fibrinolytic activity were pooled, concentrated using the Amicon stirred cell as above, and dialyzed against several changes of Mono Q buffer A (comprising 20 mM Tris-HCl, pH 8) overnight. A volume corresponding to about 18 mg protein was filtered through a 0.2 µm membrane and applied to the Mono Q column. Venom proteins were eluted from this column using a gradient elution protocol as follows: (a) 10 min isocratically at 100% Mono Q buffer A; (b) 90 min using a linear gradient to 20% Mono Q buffer B (comprising 20 mM Tris-HCl, 500 mM NaCl, pH 8); (c) 5 min linear gradient to 100% Mono Q buffer B; and (d) 5 min isocratically at 100% Mono Q buffer B. Flow rate through the column was maintained at 4 mL/min, and 2 mL fractions were collected. As above, fractions were monitored spectrophotometrically using absorbance at 280 nm, and analyzed for fibrinolytic activity and by SDS-PAGE.

This purification protocol resulted in a fibrolase preparation purified from other proteins originally present in snake venom. SDS-PAGE analysis of Mono Q column fractions having fibrinolytic activity showed purification to homogeneity, comprising a single band having an apparent molecular weight of about 23 kD. Further analysis, however, revealed that native fibrolase purified using this scheme consisted of two isoforms, detectable using extremely narrow range (pH 6.67–6.9) isoelectric focusing gel electrophoresis. The two isoforms of fibrolase were separated using a weak cationic exchange HPLC protocol, as follows.

Approximately 9 mg of protein from the Mono Q fraction pool was dialyzed against CM buffer A (comprising 30 mM 2-(N-morpholino)-ethansulfonic acid, sodium salt (NaMES), pH 6.4) and concentrated using the Amicon stirred cell. The sample was filtered through a 0.2 µm membrane and applied to a 250 mm carboxymethyl cellulose HPLC column (SynChropak CM 300, SynChrom; 10 mm internal diameter). Fibrolase isoform proteins were eluted from this column using a gradient elution protocol as follows: (a) 10 min isocratically at 100% CM 300 buffer A; (b) 95 min using a linear gradient to 30% CM 300 buffer B (comprising 30 mM NaMES, 500 mM NaCl, pH 6.4); (c) 40 min linear gradient to 100% CM 300 buffer B; and (d) 10 min isocratically at 100% CM 300 buffer B. Flow rate through the column was maintained at 2.4 mL/min, and 1.2 mL fractions were collected.

To completely resolve the isoforms, pooled fractions containing each of the isoforms fib1 and fib2 were dialyzed against CM 300 buffer A, reapplied to the column and eluted as described. Fractions containing fibrinolytic activity arising from each of the fibrolase isoforms were pooled, concentrated and exchanged into a buffer comprising 20 mM HEPES, 50 mM NaCl, pH 7.2, diluted (or concentrated) to a concentration of about 1 mg/mL, and stored at −80° until use. Protein concentration was determined using a commercially-available assay (BCA, Pierce Chemical Co., Rockford, Ill.).

Alternatively, recombinant fibrolase can be produced using the methods of European Patent Application EP 323722 and Loayza et al. (Ibid.), the teachings of these references being incorporated by reference herein.

EXAMPLE 2

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluorophosphate/hydroxybenzotriazole (HBTU/HOBT), and using p-hydroxymethylphenoxy-methylpolystyrene (HMP) resin for carboxyl-terminus acids or Rink amide resin for carboxyl-terminus amides. Resin-bound products were routinely cleaved using a solution comprised of trifluoroacetic acid, water, thioanisole (if an arginine residue comprises the peptide), ethanedithiol, and triethylsilane, prepared in ratios of 100:5:5:2.5:2 for 0.5–3 h at room temperature.

Where appropriate, N-terminal acetyl groups were introduced by treating the free N-terminal amino peptide bound to the resin with 20% v/v acetic anhydride in NMP (N-methylpyrrolidinone) for 30 min. Where appropriate, 2-chloroacetyl and 2-bromoacetyl groups were introduced either by using the appropriate 2-halo-acetic acid as the last residue to be coupled during SPPS or by treating the N-terminus free amino peptide bound to the resin with either the 2-halo-acetic acid/diisopropylcarbodiimide/N-hydroxysuccinimide in NMP or the 2-halo-acetic anhydride/diisopropylethylamine in NMP. Where appropriate, 2-haloacetylated peptides were cyclized by stirring an 0.1–1.0 mg/mL solution in phosphate or bicarbonate buffer (pH 8) containing 0.5–1.0 mM EDTA for 4–48 hours, followed by acidification with acetic acid, lyophilization and HPLC purification. Where appropriate, Cys—Cys disulfide bond cyclizations were performed by treating the precursor cysteine-free thiol peptides at 0.1 mg/mL in pH 7 buffer with aliquots of 0.006M $K_3Fe(CN)_6$ until a stable yellow color persisted. The excess oxidant was reduced with excess cysteine, the mixture lyophilized and then purified by HPLC.

Where appropriate, the amino acids 4-amidinophenylalanine and L-(S-3aminopropyl) cysteine are prepared using the protocol of Pearson et al., 1996, *J. Med. Chem.* 39: 1372–1382, incorporated by reference herein.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or electrospray mass spectrometry (ESMS).

EXAMPLE 3

Crosslinking Fibrolase with Chemical Crosslinking Agents

1. Crosslinking Fibrolase with S-GMBS via a Primary Amine

Fibrolase isoform 2 (fib2) was prepared as described in Example 1. N-(γ-maleimidobutyryloxy) sulfosuccinimide ester (S-GMBS, shown in FIG. 1 and obtained from Pierce) was dissolved in water to a final concentration of 25 mM. Fibrolase and S-GMBS were combined at a 1:20 molar ratio in a total volume of 1 mL, and allowed to react for 30 min at room temperature. After this reaction time, excess S-GMBS was removed using an Amicon Centricon-10 centrifugal concentrator. The reaction was diluted with an additional 1 mL of fibrolase dilution buffer, applied to the concentrator and centrifuged until the volume was reduced to about 200 μL. An additional 1.8 mL buffer was added and the volume again reduced to 200 μL by centrifugation. This protocol was repeated until a volume of about 5 mL had been passed through the concentrator, corresponding to about a 1:1000 dilution of the reagents comprising the fibrolase:S-GMBS reaction mixture. The final retentate from the concentrator was diluted with buffer to a final volume of 1 mL, and the fibrolase concentration determined to be 0.84 mg/mL using the BCA reagent and protocol (Pierce). Coupling reactions (described below) were performed within one hour after chemical crosslinking.

Figure 2:
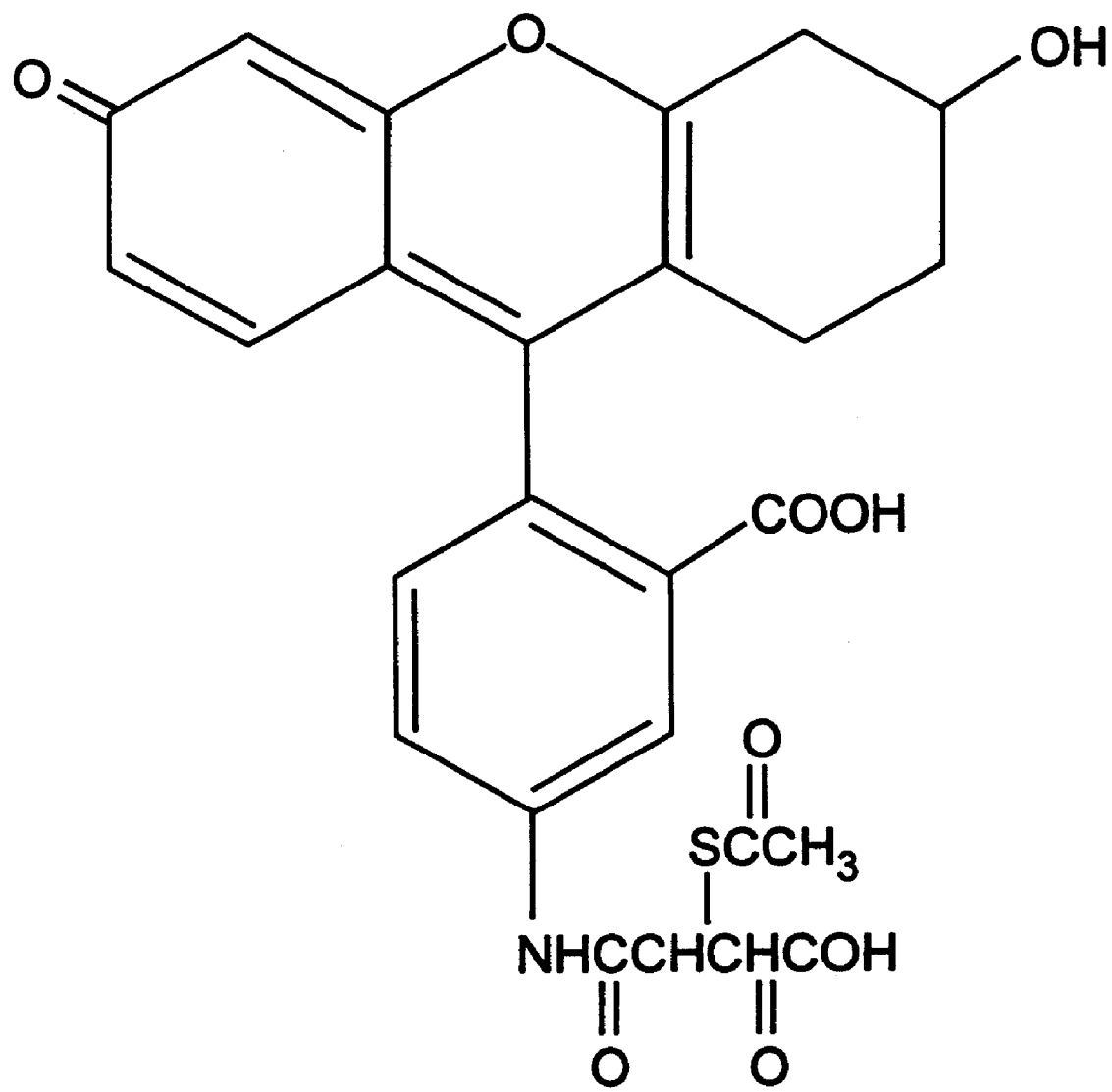
FIG. 2 shows the chemical structure of a fluorescent detection reagent (SAMSA fluorescein) used to determine the extent of chemical adduct formation between fibrolase and S-GMBS.

The extent of S-GMBS adduction to fibrolase was determined using a fluorescent detection reagent (SAMSA fluorescein, FIG. 2, obtained from Molecular Probes, Eugene Oreg.). This reagent (after strong base activation) forms a covalent linkage with thiol-reactive groups on protein modification reagents such as S-GMBS. The absorbance and fluorescent properties of SAMSA-fluorescein have been extensively characterized, which permits quantitation of the number of SAMSA-fluorescein adducts formed per fibrolase molecule, which in turn provides an accurate estimate of the average number of crosslinking agents that have been covalently linked to each fibrolase molecule. (Fibrolase contains no free sulfhydryl groups that could react with SAMSA-fluorescein.)

SAMSA-fluorescein was activated by incubation of 1 mg of the reagent in 100 μL 0.1M NaOH for 15 min at room temperature. The solution was then neutralized by the addition of 14 μL of 6M HCl buffered with 200 μL 0.5M sodium phosphate, pH 7. An aliquot of S-GMBS crosslinked fibrolase was then combined with activated SAMSA-fluorescein at a 1:10 molar ratio and incubated at room temperature for 30 min. Unbound SAMSA-fluorescein was removed as described above using a Centricon concentrator unit having a 3000 dalton molecular weight cut-off; ten volumes of buffer were exchanged with the SAMSA-fluorescein treated fibrolase reaction mixture. After concentration, the absorbance of crosslinked protein-SAMSA fluorescein was determined at 495 nm. Based on an extinction coefficient of 80,000 $cm^{-1}M^{-1}$, the number of free S-reactive maleimide groups from S-GMBS covalently linked to fibrolase was calculated to be 1.7 per molecule of fibrolase. This assay also demonstrates that there were 1.7 free maleimide groups per fibrolase molecule available for reaction with peptide (as described below). Control reactions were performed using buffer containing no fibrolase, as well as buffer containing uncrosslinked fibrolase, each of which provided a determination of non-specific background fluorescence.

2. Crosslinking Fibrolase with SPDP and S-SMPT

Figure 4:
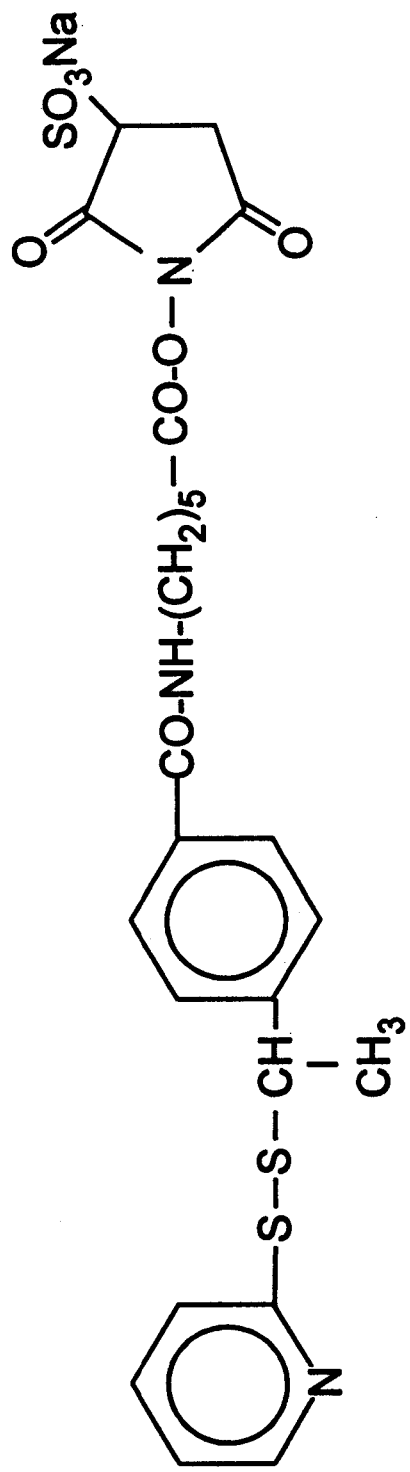
FIG. 4 illustrates the reaction scheme for the conjugation of fibrolase with a specific binding peptide of the invention using sulfosuccinimidyl-6-(α-methyl-α-(2-pyridyldithio) toluamido) hexonate (S-SMPT).

Fibrolase isoform 2 (fib2) was prepared as described in Example 1. A solution of fibrolase at a concentration of 2.6 mg/1.2 mL in 50 mM HEPES, 100 mM NaCl, pH 7.5 was treated with a 10-fold molar excess of N-succinimidyl-3-(2-pyridyldithio) propionate (SPDP, FIG. 3) or sulfosuccinimidyl-6-(α-methyl-α-(2-pyridyldithio) toluamido) hexonoate (S-SMPT, FIG. 4). (Stock solutions of each of these reagents were prepared at a concentration of 20 mM in dimethylsulfoxide.) Each mixture of reagent and fibrolase was stirred gently at room temperature for 30 min. Excess crosslinking reagent was removed by gel filtration using a Sephadex G-25 column or by centrifugation using the Centricon-10 concentrator as described above. Final protein concentration was determined using the BCA reagents and protocol.

Crosslinking efficiency of both SPDP and S-SMTP was determined by the production of pyridine-2-thione from crosslinked fibrolase after treatment with dithiothreitol. An aliquot of crosslinked fibrolase (220 μg in 1.2 mL) was treated with 0.1 mL 25 mM dithiothreitol at room temperature for 30 min. The amount of pyridine-2-thione released from the SPDP and S-SMTP crosslinking agents was detected spectrophotometrically at 343 nm, and the corresponding amount of each crosslinker covalently linked to fibrolase calculated using the extinction coefficient of pyridine-2-thione, 80,800 $cm^{-1}M^{-1}$. Using this assay, the crosslinking efficiency of both SPDP and S-SMTP were found to be nearly identical, there being 1.7 mol of either crosslinker per mol fibrolase protein.

EXAMPLE 4

Coupling Crosslinked Fibrolase with Peptide

1. Coupling Peptide with S-GMBS Crosslinked Fibrolase

Peptide (P734; the structure of which is shown below) was coupled to S-GMBS crosslinked fibrolase as follows. Peptide was added to crosslinked fibrolase at a molar ratio of 5:1 peptide:crosslink ends (equivalent to a molar ratio of 5:1.7 peptide:fibrolase for the crosslinked fibrolase preparations of Example 3). Lyophilized peptide was slowly added to a stirred fibrolase solution to permit peptide to slowly and completely dissolve. Reaction was performed under a gentle stream of nitrogen for an initial 30 min, and then the reaction mixture was capped and incubated at room temperature for 15 h. After this incubation, excess unconjugated peptide was removed from the conjugated fibrolase using a centrifugal concentrator having a 10,000 dalton molecular weight cutoff. An aliquot of the final conjugate was tested with SAMSA-fluorescein to determine the extent of unconjugated crosslinked fibrolase. This assay determined that an average of 1.7 mol peptide were adducted per mol fibrolase, indicating that essentially all of the free maleimide reactive groups on the crosslinked fibrolase had been conjugated with peptide.

P734=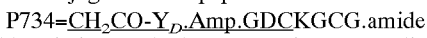.amide

Abbreviations and other conventions are as disclosed herein.

2. Coupling Peptide with SPDP- and S-SMPT-Crosslinked Fibrolase

Peptide (P734) was coupled to SPDP and S-SMTP crosslinked fibrolase as follows. Peptide was added to crosslinked fibrolase at a molar ratio of 2:1 peptide:crosslink ends (equivalent to a molar ratio of 2:1.7 peptide:fibrolase for the crosslinked fibrolase preparations of Example 3). Lyophilized peptide was slowly added to a stirred fibrolase solution to permit peptide to slowly and completely dissolve. Reaction was performed under a gentle stream of nitrogen for an initial 5 min, then the reaction mixture was capped and incubated at room temperature overnight. After this incubation, excess unconjugated peptide was removed from the conjugated fibrolase using a centrifugal concentrator having a 10,000 dalton molecular weight cutoff. An aliquot of the final conjugate was tested with SAMSA-fluorescein to determine the extent of unconjugated crosslinked fibrolase. This assay determined that an average of 1.7 mol peptide were adducted per mol fibrolase, indicating that essentially all of the free maleimide reactive groups on the crosslinked fibrolase had been conjugated with peptide.

3. HPLC Purification of Fibrolase:Peptide Conjugates

Alternatively, peptide:fibrolase conjugates were purified by HPLC as follows. For example, SPDP crosslinked conjugates were applied to a 200 mm cation exchange column (Poly Cat A, Western Analytical Products, Inc., Temecula, Calif.) in NaMES buffer at a flow rate of 1 mL/min. Conjugates were eluted from the column using an elution gradient of 0 to 30% elution buffer B (comprising 30 mM NaMES and 0.3M NaCl, pH 6.4) over 95 min, followed by 40 min elution with 100% elution buffer B.

Results of this purification protocol are shown in FIG. 5. Panel A illustrates the elution profile of unconjugated fibrolase isoform 2 control, which eluted from the column at 29.9 min, and Panel B shows the elution profile of unconjugated peptide, which eluted from the column at 66.7 min. The elution profile of fibrolase crosslinked to SPDP showed two peaks: a first peak at 6.8 min representing PDP-fibrolase, and a second peak at 29 min corresponding to unmodified fibrolase (Panel C). Peptide-fibrolase conjugates eluted from the column as shown in Panel D at 6.3 min, while unconjugated fibrolase eluted at 29 min as previously described. The amount of peptide:fibrolase conjugate obtained using this protocol was 1.46 mg from a starting amount of 2.6 mg fibrolase, an overall yield of 56.5%.

The chemical identity of the conjugate was determined by amino acid composition analysis. Conjugate samples (33–50 μg) were hydrolyzed in 6N HCl for 90 min at 150° C. The hydrolysates were derivatized with phenylisothiocyanate and analyzed using an automated amino acid analyzer (Model 420A, obtained from Applied Biosystems, Inc., Foster City, Calif.). Analysis was performed in triplicate on a 2.1×220 mm PTC-18 HPLC column at a flow rate of 300 mL/min using an ultraviolet detector set at 254 nm. Amino acid composition analyses were performed in triplicate.

Figure 6A:
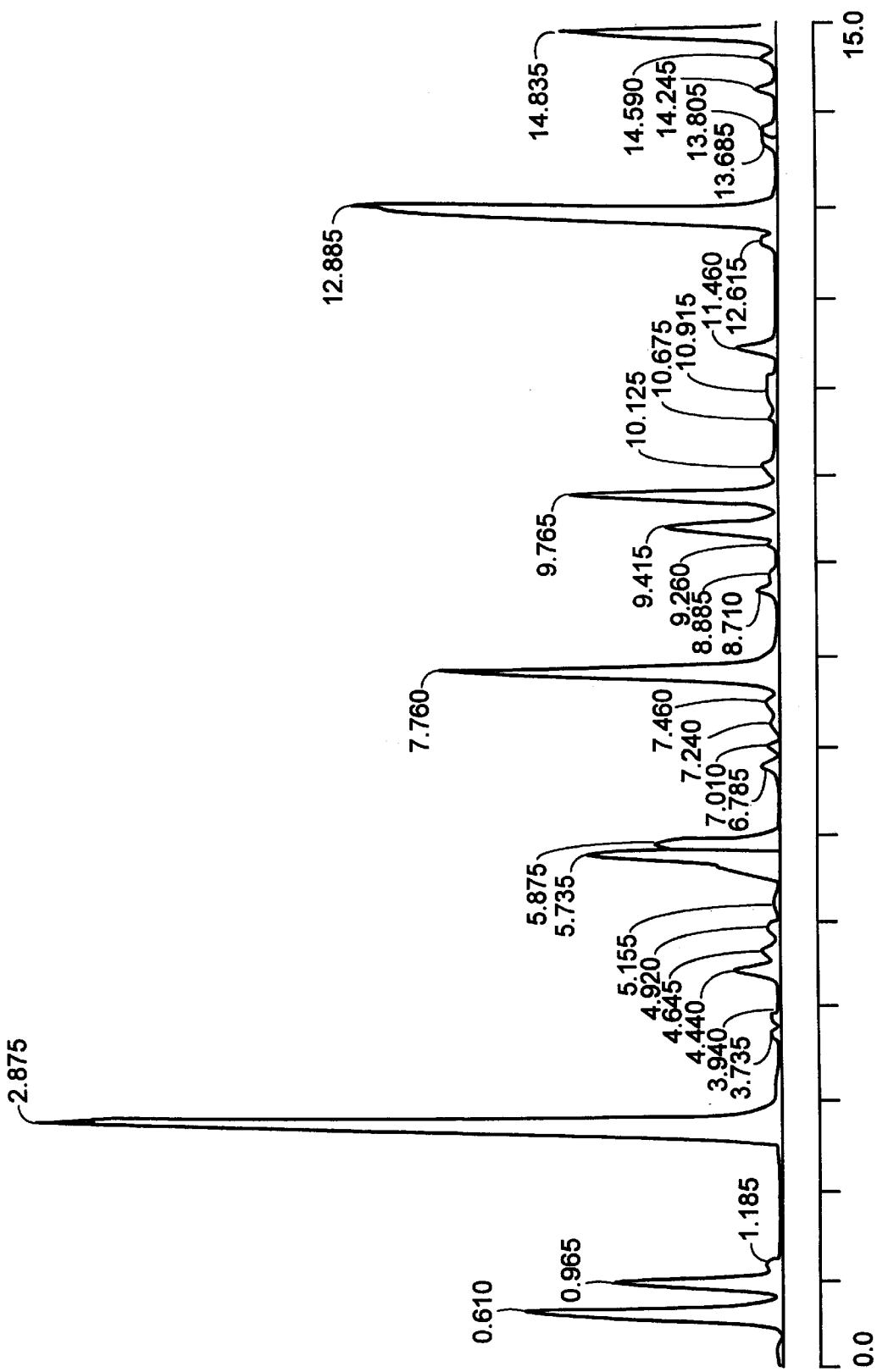
FIG. 6 shows the results of amino acid composition analysis of peptide P734 (Panel A), fibrolase (Panel B), and fibrolase:peptide P734 conjugated crosslinked with SPDP (Panel C).
Figure 6B:
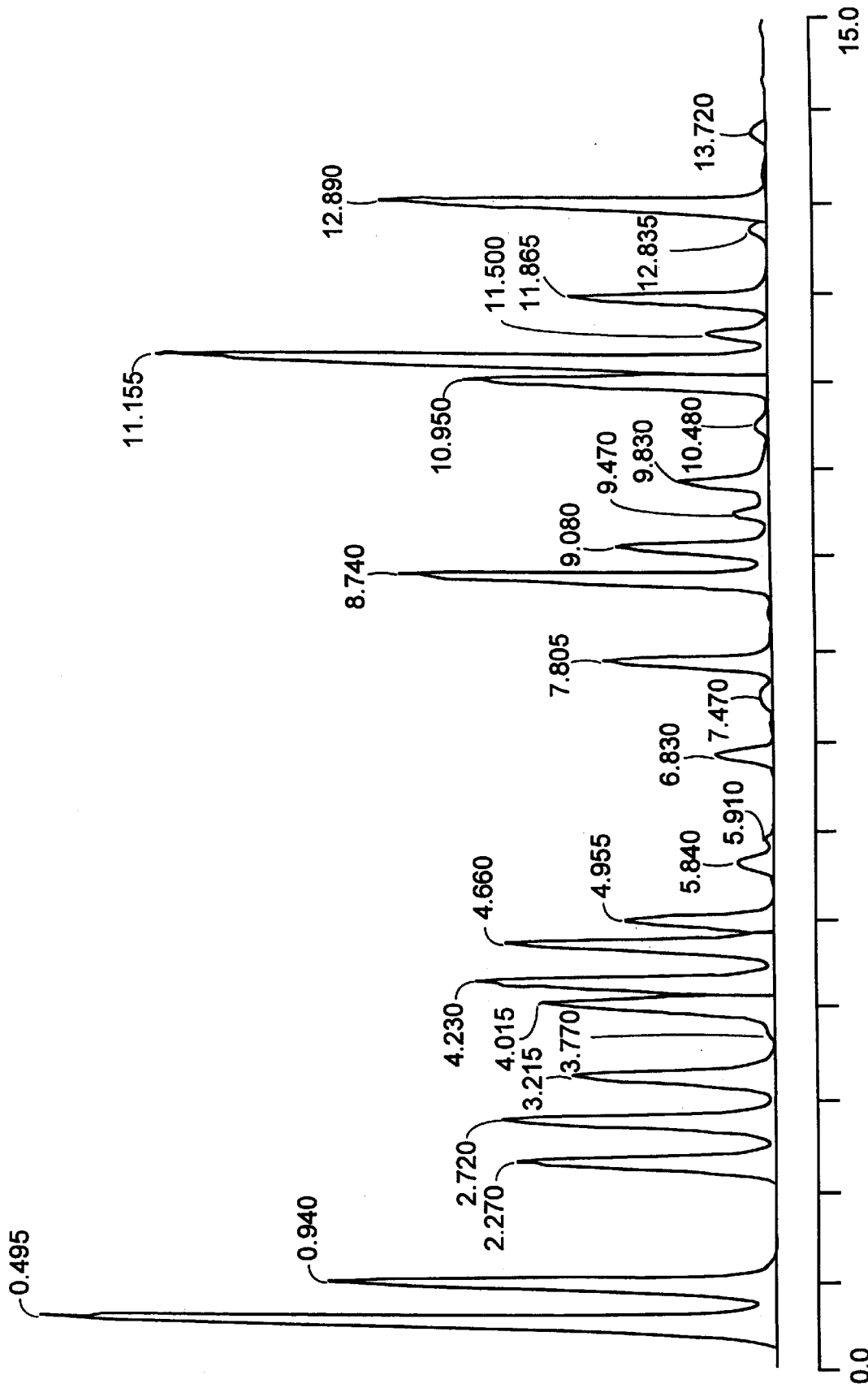
Figure 6C:
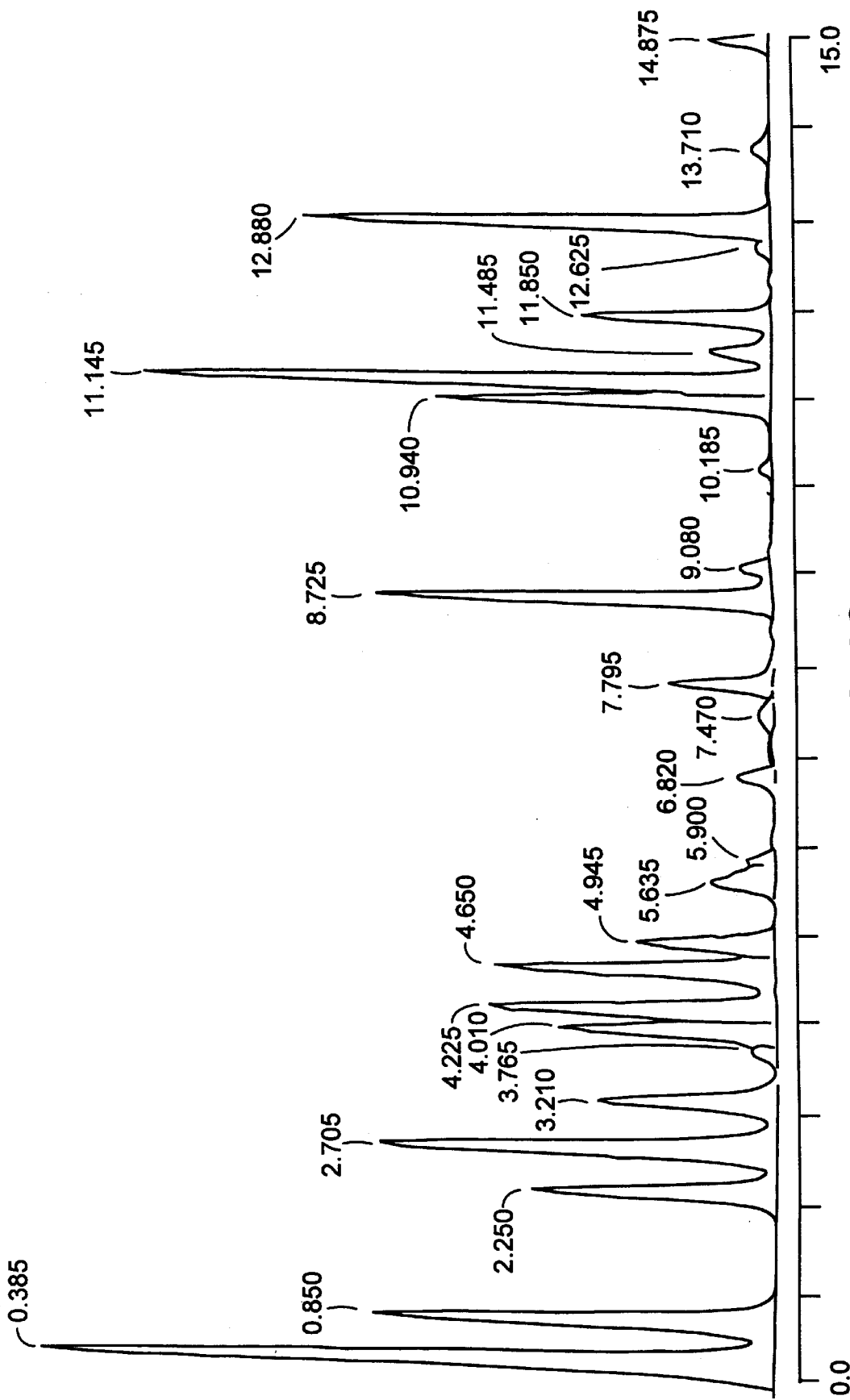

The results of these analyses are shown in Table I and in FIG. 6. Fibrolase is composed of 203 amino acids (as described in Randolph et al., 1992, *Prot. Sci.* 1: 590–600), and the peptide is made up of 9 amino acids. A unique arginine derivative (shown as peak 14.8 min in FIG. 6) is derived from the peptide; observation of this peak in the purified conjugate confirmed peptide:fibrolase conjugation at a molar ratio of from about 1:1 to about 2:1.

EXAMPLE 5

Proteolytic Activity of Peptide:Fibrolase Conjugates

The proteolytic activity of peptide:fibrolase conjugates was determined using two substrates: azocasein (to determine non-specific protease activity) and fibrin (to determine fibrinolytic activity and to compare this activity between purified fibrolase and the peptide:fibrolase conjugate). These assays were performed as follows.

Azocasein assays were performed as described in Retzios et al. (1990, *Prot. Express. Purific.* 1: 33–39). Briefly, azocasein was prepared by dissolving 2.5 g azocasein (Cal BioChem, San Diego, Calif.) in 50 mL of a 1% solution of $NaHCO_3$. This solution was gradually heated to 60° C. with stirring until the protein was totally dissolved. This solution was dialyzed overnight against 4 L of a 1% $NaHCO_3$ solution, and the protein precipitated by the addition of an equal volume of 10% trichloroacetic acid (TCA). Protein was collected by centrifugation, the supernatant discarded and the protein pellet resuspended in 50 mL of a 1% solution of $NaHCO_3$. This solution was again dialyzed overnight against 4 L of a 1% $NaHCO_3$ solution.

In performing the assay, 1 mL of the above azocasein reagent solution was combined with 50 μL of the sample and incubated at 37° C. for 30 min. After this incubation, 1 mL of a 1.16M perchloric acid solution was added. The reaction mixture was centrifuged on a tabletop centrifuge for 10 min, and absorbance at 390–440 nm was determined against the appropriate sample blank. Proteolytic activity was calculated using a standard curve of activity versus absorbance.

TABLE I

| AMINO ACID | FIBROLASE | | CONJUGATE | | PEPTIDE | |
|---|---|---|---|---|---|---|
| | Obs. | Exp. | Obs. | Exp. | Obs. | Exp. |
| Asx | 31 | 31 | 37 | 37 | 1 | 1 |
| Glx | 20 | 20 | 18 | 18 | 1 | |
| Ser | 12 | 12 | 14 | 14 | | |
| Gly | 12 | 12 | 15 | 15 | 3 | 3 |
| His | 10 | 10 | 10 | 10 | | |
| Arg | 1 | 9 | 9 | 9 | | |
| Thr | 13 | 13 | 16 | 16 | | |
| Ala | 10 | 11 | 10 | 10 | | |
| Pro | 6 | 5 | 5 | 5 | | |
| Tyr | 5 | 5 | 5 | 5 | 1 | 1 |
| Val | 11 | 14 | 12 | 12 | | |
| Met | 7 | 6 | 6 | 6 | | |
| Cys | 4 | 6 | 6 | 6 | 1 | 2 |
| Ile | 9 | 12 | 9 | 9 | | |
| Leu | 19 | 21 | 1 | 18 | | |
| Phe | 6 | 6 | 6 | 6 | | |
| Lys | 7 | 7 | 8 | 8 | 1 | 1 |
| Trp | ND | 3 | ND | 3 | | |
| Arg Deriv. | — | — | — | — | 1 | 1 |
| Total | | 203 | | 208 | | 9 |

Fibrinolytic activity was detected using a fibrin plate assay described in Bajwa et al. (1980, *Toxicon* 18: 285–289). Briefly, a fibrin plate was prepared by pipetting a fibrinogen solution (6 mL 1.65% human fibrinogen in 0.07M ammonium sulfate, 50 mM sodium barbital, 93 mM NaCl, 1.66 mM $CaCl_2$, and 0.69 mM $MgCl_2$, pH 7.5) onto a 90×15 mm petri dish after mixing with 0.2 mL of a topical thrombin solution (20 NIH units/mL in 150 mM NaCl, pH 7.5; obtained from Parke-Davis, Detroit, Mich.) containing 0.25% gelatin (Difco labs, Detroit, Mich.). Plates were allowed to stand at room temperature for at least 30 min on a level surface to form the fibrin layer. Small (2 mm diameter) holes comprising sample wells were made in the fibrin layer, spaced at 1.5 cm intervals on the plate. Samples were added to the sample wells in 10 μL, and the plates incubated at 37° C. for 18 h. Fibrin plate clearance was determined as the increase in diameter of the sample well due to fibrinolytic activity of the sample. Alternatively, a 24-well plate was used to perform this assay, wherein each well contains 300 μL of a fibronogen solution, into which is added 10 μL of a thrombin solution to initiate fibrin formation.

The results of these assays are shown in Table II. The proteolytic activities of fibrolase, PDP-fibrolase and peptide:fibrolase conjugate are shown. The SPDP modification of two ε-amino groups in fibrolase did not appear to have any significant effect on fibrolase activity in either assay. The derivatized fibrolase in each instance retained over 90% of the proteolytic activity of native fibrolase. Subsequent conjugation of PDP-fibrolase with P734 peptide also produced no dramatic change in proteolysis activity, the conjugate displaying 79–82% of native fibrolase activity in both assays. Results similar to these results (obtained with a crosslinking agent having a 6.8 Å spacer carbon chain) were obtained with S-SMPT crosslinked conjugates (wherein the SMPT moiety has a 20 Å spacer arm) and with S-GMBS crosslinked conjugates (which showed no reduction in proteolytic activity in either assay). These results demonstrate that derivatization of fibrolase isoform 2 with a variety of chemical crosslinking agents and conjugation with a platelet-specific peptide does not adversely affect the proteolytic, and more importantly, the fibrinolytic activity of fibrolase.

TABLE II

| ENZYME | SPECIFIC ACTIVITY | | | |
|---|---|---|---|---|
| | Azocasein (U/mg) | %[a] | Human Fibrin (U/mg) | %[a] |
| Fibrolase | 1.22 ± 0.05 | 100 | 32.2 ± 2.5 | 100 |
| PDP fibrolase | 1.12 ± 0.03 | 92 | 29.6 ± 2.5 | 92 |
| PDP conjugate | 1.00 ± 0.05 | 82 | 26.4 ± 2.5 | 82 |
| S-SMPT conjugate | 0.98 ± 0.05 | 80 | 27.0 ± 2.5 | 84 |
| S-GMBS conjugate | 1.20 ± 0.05 | 98 | 35.1 ± 1.8 | (100) |

One azocasein unit was defined as the change in absorbance at 390 nm/min
One fibrinolysis unit was defined as the area of lysis of 1.0 μg in mm$^2$
a = percentage of fibrolase activity

EXAMPLE 6

Platelet Aggregation Inhibition Assays of Peptide:Fibrolase Conjugates

Platelet aggregation studies were performed essentially as described by Zucker (1989, *Methods in Enzymol.* 169: 117–133). Briefly, platelet aggregation was assayed with or without putative platelet aggregation inhibitory compounds using fresh human platelet-rich plasma (PRP), comprising 250,000 platelets per microlitre. Whole human blood (36 mL) were freshly drawn from volunteers who were medication-free for at least 2 weeks prior to blood draw. Blood was drawn into 4 mL of a 0.1M sodium citrate solution and centrifuged (150 g for 20 min at 22° C.) to pellet red blood cells. The supernatant, comprising PRP, was removed and the remaining blood recentrifuged at 8000 g for 10 min to produce platelet-poor plasma (PPP; used to dilute the PRP to a final concentration of 250,000 platelets/ μL). Alternatively, PPP was prepared by centrifugation of PRP for 1 min in a tabletop microcentrifuge. PPP is also used as a negative control for platelet aggregation.

Platelet aggregation was induced by the addition at 37° C. of a solution of adenosine diphosphate to a final concentration of 20 micromolar, and the extent of platelet aggregation monitored using a four channel aggregometer (Model IV Plus, Helena Laboratories, Beaumont, Tex.). The concentrations of platelet aggregation inhibitory compounds used were varied from 0.1 to 500 μg/mL, and these compounds were added to PRP immediately prior to (about 1 min before) addition of the ADP solution used to induce platelet aggregation. The concentration of inhibitor that reduced the extent of platelet aggregation by 50% (defined as the $IC_{50}$) was determined from plots of inhibitor concentration versus extent of platelet aggregation. Inhibition curves for a variety of disintegrins comprising the peptide sequence RGD was determined for each batch of platelets tested as positive controls.

The results of these experiments are shown in Table III. Native fibrolase was determined to have an $IC_{50}$ value of greater than 1300 nM, while the P734 peptide showed an $IC_{50}$ value of 67 nM. P734 conjugated with S-SMPT was determined to have an $IC_{50}$ of 300 nM, while the S-GMBS crosslinked embodiment showed an $IC_{50}$ of 97 nM. These results illustrate that the peptide:fibrolase conjugates of the invention retain the capacity to inhibit platelet aggregation in vitro, a property strongly correlated with platelet binding and antithrombotic activity in vivo.

TABLE III

| COMPOUND | $IC_{50}$ (nM) |
|---|---|
| Fibrolase | 1300 |
| P734 peptide | 67 |
| P734-SPDP-fibrolase conjugate | 300 |
| P734-S-SMPT-fibrolase conjugate | 300 |
| P734-S-GMBS-fibrolase conjugate | 97 |

It should be understood that the foregoing disclosure emphasizes certain specific embodiments of the invention and that all modifications or alternatives equivalent thereto are within the spirit and scope of the invention as set forth in the appended claims.

What is claimed is:

1. A thrombolytic agent comprising fibrolase chemically crosslinked to a peptide selected from the group consisting of:

$CH_2CO.Y_D.Apc.GDCGGC_{Acm}GC_{Acm}GGC$.amide;
$CH_2CO.Y_D.Apc.GDCKGC_{Acm}GC_{Acm}GGC$.amide;
$C_{Acm}GC_{Acm}GGRGDSC$ (SEQ ID NO: 3);
$C_{Acm}GC_{Acm}GGRGDGGRGDSC$ (SEQ ID NO: 4);
$C_{Acm}GC_{Acm}GGRGDGGRGDGGRGDSC$ (SEQ ID NO: 5);
$C_{Acm}GC_{Acm}RRRRRRRRRGDVC$ (SEQ ID NO: 6);
$CGRGDVKC_{Acm}GC_{Acm}$.amide (SEQ ID NO: 7);
$CGRGDVC_{Acm}GC_{Acm}$.amide (SEQ ID NO: 8);
$CGRGDVRGDFKC_{Acm}GC_{Acm}$.amide (SEQ ID NO: 9);
$CGRGDVRGDFC_{Acm}GC_{Acm}$.amide (SEQ ID NO: 10);
acetyl-$G.Apc.GDV.Apc.GDFKC_{Acm}GC_{Acm}.GGC$amide (SEQ ID NO: 11);
$G.Apc.GDV.Apc.GDFKC_{Acm}GC_{Acm}.GGC$amide (SEQ ID NO: 11);
$G.Apc.GDVKC_{Acm}GC_{Acm}GGC$.amide (SEQ ID NO: 12);
$CC_{Acm}GC_{Acm}GGRGDS$ (SEQ ID NO: 13);
acetyl-$RRARGDDLDC_{Acm}GC_{Acm}GGC$.amide (SEQ ID NO: 14);
$GRGDFGGCAC_{Acm}$ (SEQ ID NO: 15);
$ma_{Bz}$-GGRGDF (SEQ ID NO: 16);
$C_{Acm}$ GGGRGDF (SEQ ID NO: 17);
$GRGDGGC_{Acm}$ (SEQ ID NO: 18);
ma-GGRGDF (SEQ ID NO: 16);
$ma_{Acm}$-GGGRGDF (SEQ ID NO: 19);
ma-RGDF (SEQ ID NO: 20);
ma-RGD;
$CH_2CO.Y_D.Apc.GDCGGC$.amide;
$CH_2CO.Y_D.Apc.GDCGGGC$.amide;
$CH_2CO.Y_D.Apc.GDCKGGGC$.amide;
$CH_2CO.Y_D.Apc.GDCGGGGC$.amide;
GGRGDSC (SEQ ID NO: 21);
GGRGDGGRGDSC (SEQ ID NO: 22);
GGRGDGGRGDGGRGDSC (SEQ ID NO: 23);
RRRRRRRRRGDVC (SEQ ID NO: 24);
CGRGDVK.amide (SEQ ID NO: 25);
CGRGDV.amide (SEQ ID NO: 26);
CGRGDVRGDFK.amide (SEQ ID NO: 27);
CGRGDVRGDF.amide (SEQ ID NO: 28);
acetyl-G.Apc.GDV.Apc.GDFKGGCamide (SEQ ID NO: 29);
G.Apc.GDV.Apc.GDFKGGCamide (SEQ ID NO: 29);
G.Apc.GDVKGGC.amide (SEQ ID NO: 30);
CGGRGDS (SEQ ID NO: 31);
acetyl-RRARGDDLDGGC.amide (SEQ ID NO: 32);

CKRARGDDMDDYC (SEQ ID NO: 33);
mmp-GGGRGDF (SEQ ID NO: 19);
acetyl-RGDC.amide (SEQ ID NO: 34);
CRGDC (SEQ ID NO: 35);
CGGGRGDF (SEQ ID NO: 17);
GRGDGGGC (SEQ ID NO: 36);
GRGDGGC (SEQ ID NO: 18);
ma$_{Acm}$-GGGRGDF (SEQ ID NO: 19);
acetyl-CNP.Apc.GDC (SEQ ID NO: 37);
CRIARGDWNDDYC (SEQ ID NO: 38);
CKFFARTVCRIARGDWNDDYCTGKSSDC (SEQ ID NO: 39);
KYGGHHLGGAKQAGDV (SEQ ID NO: 40);
CH$_2$CO-Y$_D$.Amp.GDCKGCG.amide)$_2$-(ε-K)GC.amide; and
CH$_2$CO-Y$_D$.Amp.GDCKGCG.amide.

2. A thrombolytic agent comprising fibrolase chemically crosslinked to a peptide having a formula:

3. A thrombolytic agent comprising fibrolase chemically crosslinked to a peptide comprising at least two copies of a sequence GPRP (SEQ ID NO:2).

4. The thrombolytic agent of any of claims 1 through 3, wherein said peptide is crosslinked with a crosslinker selected from the group consisting of N-succinimidyl-2-(2-pyridyldithio) propionate, N-(γ-maleimidobutyryloxy) sulfosuccinimide ester, succinimidyl 4-(p-maleimidophenyl) butyrate, sulfosuccinimidyl-4-(p-maleimidophenyl) butyrate, 4-succinimidyloxycarbonyl-methyl-α-(2-pyridyldithio)toluene, N-hydroxysuccinimidyl-2,3-dibromopropionate, N-succinimidyl-(4-iodoacetyl)-aminobenzoate, sulfosuccinimidyl-(4-iodoacetyl)-aminobenzoate, succinimidyl-4-(N-maleimidomethyl) cyclohexane-1-carboxylate, sulfosuccinimidyl-4-(N-maleimidomethyl)cyclohexane-1-carboxylate, N-(γ-maleimidobutyryloxy) succinimide ester, m-maleimidobenzenyl-N-hydroxysuccinimide ester, m-maleimidobenzenyl-N-hydroxysulfosuccinimide ester, sulfosuccinimidyloxycarbonyl-6-(α-methyl)-α-(2-pyridyldithio) toluamide hexanoate, and sulfosuccinimidyl-6-(α-methyl-α-(2-pyridyldithio)toluamido)hexanoate.

5. The thrombolytic agent of any of claims 1 through 3, wherein the fibrolase is isolated from *Agkistrodon contortrix contortrix* venom and identified as EC 3.4.24.72.

6. A method of lysing a thrombus in a mammalian body comprising the step of administering to said body a therapeutically effective amount of the thrombolytic agent of any of claims 1 through 3.

7. The thrombolytic agent of any of claims 1 through 3, further comprising a gamma-emitting radioisotope.

* * * * *

UNITED STATES PATENT AND TRADEMARK OFFICE
CERTIFICATE OF CORRECTION

| | |
|---|---|
| PATENT NO. | : 5,951,981 |
| APPLICATION NO. | : 08/753781 |
| DATED | : September 14, 1999 |
| INVENTOR(S) | : Francis S. Markland, Jr. et al. |

It is certified that error appears in the above-identified patent and that said Letters Patent is hereby corrected as shown below:

Title Page (73)
      Page 1, ASSIGNEE insert -- University of Southern California, Los Angeles, C.A. --

Signed and Sealed this

Eighth Day of July, 2008

JON W. DUDAS
*Director of the United States Patent and Trademark Office*